United States Patent
Li et al.

(10) Patent No.: US 12,237,212 B2
(45) Date of Patent: Feb. 25, 2025

(54) IMPLANTABLE ALL DIAMOND MICROELECTRODE AND FABRICATION METHOD

(71) Applicants: Board of Trustees of Michigan State University, East Lansing, MI (US); Fraunhofer USA, East Lansing, MI (US)

(72) Inventors: Wen Li, Okemos, MI (US); Yue Guo, Lansing, MI (US); Thomas Schuelke, Pinckney, MI (US); Michael Becker, East Lansing, MI (US); Robert Rechenberg, Vermontville, MI (US); Cory Rusinek, Okemos, MI (US)

(73) Assignees: Board of Trustees of Michigan State University, East Lansing, MI (US); Fraunhofer USA, East Lansing, MI (US)

( * ) Notice: Subject to any disclaimer, the term of this patent is extended or adjusted under 35 U.S.C. 154(b) by 640 days.

(21) Appl. No.: 16/650,485

(22) PCT Filed: Sep. 27, 2018

(86) PCT No.: PCT/US2018/053168
§ 371 (c)(1),
(2) Date: Mar. 25, 2020

(87) PCT Pub. No.: WO2019/067748
PCT Pub. Date: Apr. 4, 2019

(65) Prior Publication Data
US 2020/0303236 A1 Sep. 24, 2020

Related U.S. Application Data

(60) Provisional application No. 62/563,980, filed on Sep. 27, 2017.

(51) Int. Cl.
*A61B 18/14* (2006.01)
*A61B 5/00* (2006.01)
(Continued)

(52) U.S. Cl.
CPC .............. *H01L 21/763* (2013.01); *A61N 1/05* (2013.01); *C23C 16/27* (2013.01); *H01L 29/04* (2013.01);
(Continued)

(58) Field of Classification Search
CPC ...... A61N 1/05; A61N 1/0551; A61N 1/0529; A61N 1/0534; A61N 1/0543;
(Continued)

(56) References Cited

U.S. PATENT DOCUMENTS 6,477,233 B1 11/2002 Ribbing et al.
2003/0100823 A1* 5/2003 Kipke .................. A61B 5/4041
607/116

(Continued)

FOREIGN PATENT DOCUMENTS

JP 2008188123 A 8/2008

OTHER PUBLICATIONS

Luong et al. "Boron-doped diamond electrode: Synthesis, characterization, functionalization and analytical applications". The Royal Society of Chemistry. (Year: 2009).*

(Continued)

*Primary Examiner* — Joseph A Stoklosa
*Assistant Examiner* — Brian M Antiskay
(74) *Attorney, Agent, or Firm* — Harness, Dickey & Pierce, PLC

(57) ABSTRACT

An electrode is provided. The electrode includes a contact pad composed of boron-doped polycrystalline diamond (BDD); a fiber core composed of BDD extending longitudinally from the contact pad from a first end that is in direct (Continued)

contact with the contact pad to an opposing second end; and a polycrystalline diamond (PCD) cladding that coats and hermetically seals the contact pad and the fiber core. A first portion of the contact pad and a second portion at or near the second end of the fiber core are not coated and hermetically sealed by the PCD cladding. A method of fabricating the electrode is also provided.

20 Claims, 14 Drawing Sheets

(51) Int. Cl.
    A61N 1/05    (2006.01)
    C23C 16/27    (2006.01)
    H01L 21/763    (2006.01)
    H01L 29/04    (2006.01)
    A61B 5/025    (2006.01)
(52) U.S. Cl.
    CPC ....... A61B 5/025 (2013.01); A61B 2562/0209 (2013.01); A61B 2562/125 (2013.01)
(58) Field of Classification Search
    CPC .. A61N 1/0565; A61N 1/3754; A61N 1/0476; A61N 1/0531; A61N 1/04; A61N 1/36017; A61B 5/291; A61B 2562/125; A61B 5/24; A61B 5/283; A61B 2562/0285; A61B 2562/046; A61B 18/14; A61B 5/0031; A61B 2562/028
    USPC ........ 600/372–373, 377–378, 393, 544–545; 607/115–118
    See application file for complete search history.

(56) References Cited

U.S. PATENT DOCUMENTS

| 2009/0248113 | A1* | 10/2009 | Nimer | A61N 1/05 607/116 |
| 2009/0325424 | A1 | 12/2009 | Aarts et al. | |
| 2013/0131485 | A1* | 5/2013 | Oh | A61B 5/24 29/829 |
| 2013/0281325 | A1 | 10/2013 | Elibol et al. | |
| 2013/0345780 | A1* | 12/2013 | Tabada | A61B 5/24 216/14 |
| 2015/0250421 | A1* | 9/2015 | Arumugam | A61B 5/287 427/2.11 |
| 2016/0287113 | A1 | 10/2016 | Hebert et al. | |
| 2017/0007813 | A1* | 1/2017 | Negi | A61B 5/6868 |
| 2018/0353750 | A1* | 12/2018 | Hetke | A61N 1/0534 |
| 2018/0368712 | A1* | 12/2018 | Gardner | C23C 16/56 |
| 2019/0282110 | A1* | 9/2019 | Li | H01L 21/02527 |

OTHER PUBLICATIONS

Long et al. "The concentration gradient of boron along the growth direction in boron doped chemical vapor deposited diamond" Materials Letters 157 (2015) 34-37. (Year: 2015).*

International Search Report and Written Opinion of the International Searching Authority regarding International Application No. PCT/US2018/053168, (Feb. 19, 2019).

Aarts, A. et al., "A 3D slim-base probe array for in vivo recorded neuron activity;" 2008 30th Annual International Conference of the IEEE Engineering in Medicine and Biology Society, pp. 5798-5801 (2008).

Bennet, K. et al., "A Diamond-Based Electrode for Detection of Neurochemicals in the Human Brain;" Frontiers in Human Neuroscience, vol. 10, No. 102, pp. 1-12 (Mar. 2016).

Blau, A., "Prospects for Neuroprosthetics: Flexible Microelectrode Arrays with Polymer Conductors;" Applied Biomedical Engineering, InTechOpen, pp. 83-122 (Aug. 2011).

Ciszewski, A. et al, "Polyeugenol-Modified Platinum Electrode for Selective Detection of Dopamine in the Presence of Ascorbic Acid;" Analytical Chemistry, vol. 71, No. 5, pp. 1055-1061 (1999).

Erdogdu, G. et al., "Voltammetric Resolution of Ascorbic Acid and Dopamine at Conducting Polymer Electrodes;" Analytical Letters, vol. 29, No. 2, pp. 221-231 (1996).

Fan, B. et al., "Large-scale, all polycrystalline diamond structures transferred onto flexible Parylene-C films for neurotransmitter sensing;" Lab on a Chip, vol. 17, No. 18, pp. 3159-3167 (Sep. 12, 2017).

Guitchounts, G. et al., "A carbon-fiber electrode array for long-term neural recording;" Journal of Neural Engineering, vol. 10, No. 4, 046016 (2013).

Herwik, S. et al., "Fabrication technology for silicon-based microprobe arrays used in acute and sub-chronic neural recording;" Journal of Micromechanics and Microengineering, vol. 19, No. 7, 074008 (2009).

Hetke, J. et al., "3-D silicon probe array with hybrid polymer interconnect for chronic cortical recording;" First International IEEE EMBS Conference on Neural Engineering, 2003. Conference Proceedings, pp. 181-184 (2003).

Kozai, T. et al., "In vivo chronic cortical recordings using novel ultra-small carbon fiber based implantable microthread ultramicroelectrodes;" Program No. 227.6, 2010 Neuroscience Meeting Planner; San Diego, CA: Society for Neuroscience (2010).

Kozai, T. et al., "Ultrasmall implantable composite microelectrodes with bioactive surfaces for chronic neural interfaces;" Nature Materials, vol. 11, No. 12, pp. 1065-1073 (Dec. 2012).

Millar, J. et al., "Electrochemical, pharmacological and electrophysiological evidence of rapid dopamine release and removal in the rat caudate nucleus following electrical stimulation of the median forebrain bundle;" European Journal of Pharmacology, vol. 109, No. 3, pp. 341-348 (Mar. 12, 1985).

Mo, J. et al, "Simultaneous Measurement of Dopamine and Ascorbate at Their Physiological Levels Using Voltammetric Microprobe Based on Overoxidized Poly(1,2-phenylenediamine)-Coated Carbon Fiber;" Analytical Chemistry, vol. 73. No. 6, pp. 1196-1202 (2001).

Park, J. et al., "Micropatterning of poly(dimethylsiloxane) using a photoresist lift-off technique for selective electrical insulation of microelectrode arrays;" Journal of Micromechanics and Microengineering, vol. 19, No. 6, 65016 (May 20, 2009).

Patel, P. et al., "Insertion of linear 8.4 mm diameter 16 channel carbon fiber electrode arrays for single unit recordings;" Journal of Neural Engineering, vol. 12, No. 4, 046009 (2015).

Philip, J. et al., "Elastic, mechanical, and thermal properties of nanocrystalline diamond films;" Journal of Applied Physics, vol. 93, No. 4, pp. 2164-2171 (Feb. 15, 2003).

Pothof, F. et al., "Comparison of the in-vivo neural recording quality of floating and skull-fixed silicon probes;" 2017 8th International IEEE/EMBS Conference on Neural Engineering (NER), pp. 158-161 (2017).

Rotter, S. et al., "Diamond CVD by a Combined Plasma Pretreatment and Seeding Procedure;" Chemical Vapor Deposition, vol. 15, No. 7-9, pp. 209-216 (Sep. 2009).

Tran, D. et al., "Investigation of mask selectivities and diamond etching using microwave plasma-assisted etching;" Diamonds and Related Materials, vol. 19, No. 7-9, pp. 778-782 (2010).

Roberts, J. et al., "Fast-Scan Cyclic Voltammetry: Chemical Sensing in the Brain and Beyond;" Analytical Chemistry, vol. 90, No. 1, pp. 490-504 (2018).

Rodeberg, N. et al., "Hitchhiker's Guide to Voltammetry: Acute and Chronic Electrodes for in Vivo Fast-Scan Cyclic Voltammetry;" ACS Chemical Neuroscience, vol. 8, No. 2, pp. 221-234 (2017).

Rusinek, C. et al., "All-diamond microfiber electrodes for neurochemical analysis;" Journal of The Electrochemical Society, vol. 165, No. 12, G3087-G3092 (Jul. 31, 2018).

Schwerdt, H. et al., "Subcellular probes for neurochemical recording from multiple brain sites;" Lab on a Chip, vol. 17, No. 6, pp. 1104-1115 (2017).

Spieth, S. et al., "A floating 3D silicon microprobe array for neural drug delivery compatible with electrical recording;" Journal of Micromechanics and Microengineering, vol. 21, No. 12, 125001 (2011).

(56) References Cited

OTHER PUBLICATIONS

Tran, D. et al., "Microwave plasma-assisted etching of diamond;" Diamond and Related Materials, vol. 17, No. 4-5, pp. 717-721 (2008).
Vahidpour, F. et al., "All-diamond functional surface micro-electrode arrays for brain-slice neural analysis;" Physica Status Solidi A, vol. 214, No. 2, 1532347 (Nov. 15, 2016).
Varney, M. et al., "All-diamond Micro-electrode Arrays for Neural Recordings and Diamond Electrochemistry;" 2010 IEEE 5th International Conference on Nano/Micro Engineered and Molecular Systems, pp. 1116-1119 (2010).
Varney, M. et al., "Polycrystalline-Diamond MEMS Biosensors Including Neural Microelectrode-Arrays;" Biosensors, vol. 1, No. 3, pp. 118-133 (Aug. 15, 2011).
Wu, K. et al., "Simultaneous determination of dopamine and serotonin on a glassy carbon electrode coated with a film of carbon nanotubes;" Analytical Biochemistry, vol. 318, No. 1, pp. 100-106 (Jul. 2003).
Zaouk, R. et al., "Introduction to microfabrication techniques;" Microfluidic Techniques: Reviews and Protocols, Methods in Molecular Biology, vol. 321, pp. 5-15 (2006).

\* cited by examiner

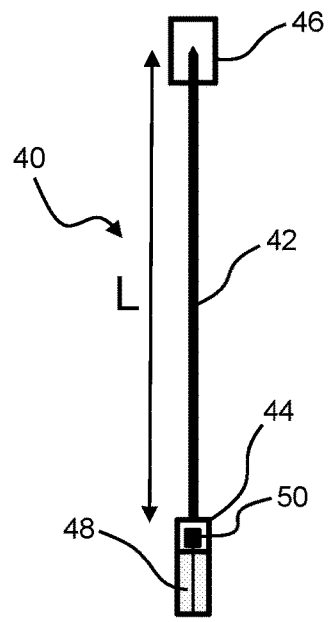
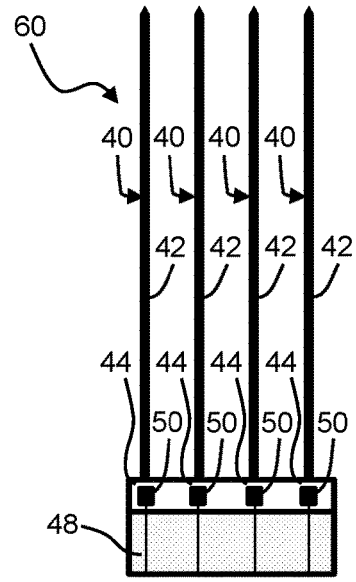
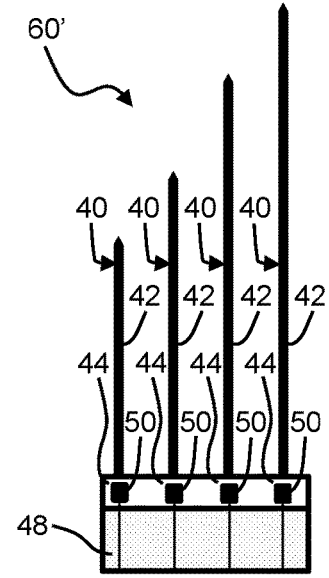
Fig. 3A                Fig. 3B                Fig. 3C
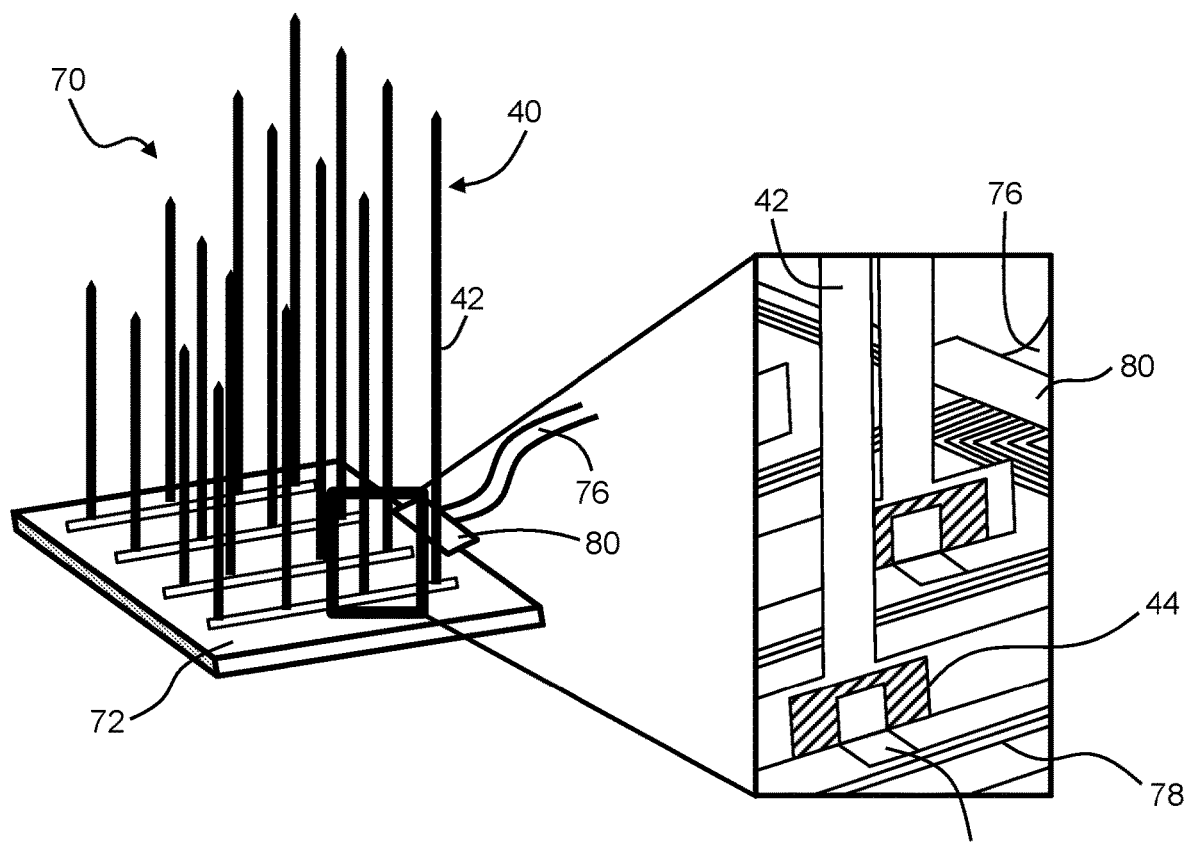
Fig. 3D

IMPLANTABLE ALL DIAMOND MICROELECTRODE AND FABRICATION METHOD

CROSS-REFERENCE TO RELATED APPLICATIONS

This application is a 371 U.S. National Phase of International Application No. PCT/US2018/053168, filed Sep. 27, 2018 which claims the benefit of U.S. Provisional Application No. 62/563,980, filed on Sep. 27, 2017. The entire disclosure of the above applications are incorporated herein by reference.

GOVERNMENT RIGHTS

This invention was made with government support under NS096637 awarded by the National Institutes of Health. The government has certain rights in the invention.

FIELD

The present disclosure relates to the design and fabrication method of micromachined, implantable, all diamond neural microelectrodes.

BACKGROUND

This section provides background information related to the present disclosure which is not necessarily prior art.

Implantable microelectrodes that can record extracellular biopotentials and neurochemical signals from small, targeted groups of neurons are critical for neuroscience research and emerging clinical applications such as brain-machine interfaces (BMIs). At present, one major challenge is to develop microelectrodes capable of recording neural activity from the same neurons for many years (greater than 70 years) with high fidelity and reliability.

Understanding the role of brain function in health and disease is one of the greatest scientific challenges. Although tremendous efforts have been made to explain how local brain regions operate, no general theory of brain function is universally accepted due to insufficient knowledge of the whole brain circuitry. Whole brain mapping with minimal invasiveness and high spatiotemporal resolution is urgently needed. This is, however, extremely challenging due to the limitations of existing recording technologies. Over the past decades a number of different microelectrode techniques, such as penetrating silicon probes and polymer probes, have been used in the attempt to record extracellular biopotentials and neurochemical signals. Such invasive devices, however, suffer from limited spatial resolution due to unpredictable current pathways and deteriorated signal quality over time due to glial scar formation. Recently, a carbon microelectrode for neural recordings, which comprises a carbon-fiber recording core and a poly(p-xylylene)-based thin-film coating was reported. Since its development, this carbon fiber-based device has been quickly adopted by many groups for use in neuroscience study because it enables a smaller implant than traditional recording microelectrodes; it is also mechanically compliant with brain tissue. However, the thin polymer package fails over the course of long-term implantation due to the porous nature of polymeric materials. Furthermore, device fabrication requires time-consuming and laborious hand alignment and assembly of carbon fibers onto contact pads, which makes it difficult for these devices to be scaled up. Therefore, new electrodes and electrode fabrication methods are needed to address the foregoing issues.

SUMMARY

This section provides a general summary of the disclosure, and is not a comprehensive disclosure of its full scope or all of its features.

In various aspects, the current technology provides an electrode having a contact pad including boron-doped polycrystalline diamond (BDD); a fiber core including BDD extending longitudinally from the contact pad from a first end that is in direct contact with the contact pad to an opposing second end; and a polycrystalline diamond (PCD) cladding that coats and hermetically seals the contact pad and the fiber core, wherein a first portion of the contact pad and a second portion at or near the second end of the fiber core are not coated and hermetically sealed by the PCD cladding.

In one aspect, the fiber core has a rectangular or square cross-sectional geometry.

In one aspect, the second end of the fiber core is blunt and the second portion is at the second end.

In one aspect, the fiber core is not coated at the second end and has a width $W_{Core}$ greater than or equal to about 0.1 µm to less than or equal to about 25 µm and a height $H_{Core}$ of greater than or equal to about 0.25 µm to less than or equal to about 10 µm.

In one aspect, the second end of the fiber core is pointed.

In one aspect, the second portion at or near the pointed second end of the fiber core that is not coated and hermetically sealed by the PCD cladding is a longitudinal surface at or near the pointed second end of the fiber core, such that the BDD fiber core is exposed at the longitudinal surface at or near the pointed second end of the fiber core.

In one aspect, the exposed BDD fiber has a surface area of greater than or equal to about 1 µm$^2$ to less than or equal to about 400 µm$^2$.

In one aspect, the PCD cladding has a thickness $T_{Clad}$ of greater than or equal to about 0.1 µm to less than or equal to about 10 µm.

In one aspect, the PCD cladding is substantially free of pinholes.

In one aspect, the BDD fiber core has a length of greater than or equal to about 0.5 mm to less than or equal to about 20 mm.

In one aspect, the BDD fiber core coated with PCD has a diameter that is smaller than the size of a neuron.

In one aspect, the current technology provides a fiber comb including at least two electrodes, wherein the BDD fiber core of each of the at least two electrodes individually has a length of greater than or equal to about 0.5 mm to less than or equal to about 20 mm, and wherein the at least two electrodes are arranged in a line.

In one aspect, the at least two electrodes are electrically coupled to a ribbon cable.

In one aspect, the current technology provides a fiber array including at least three electrodes, wherein the BDD fiber core of each of the at least three electrodes individually has a length of greater than or equal to about 1 mm to less than or equal to about 10 mm, and wherein the at least three electrodes are arranged in a three-dimensional pattern.

In one aspect, the at least three electrodes extend from, and are electrically coupled to, a circuit substrate.

In various aspects, the current technology further provides an electrode including at least one individual electrode having a contact pad including boron-doped polycrystalline diamond (BDD); a fiber core including BDD extending longitudinally from the contact pad from a first end that is in direct contact with the contact pad to an opposing second end; and a polycrystalline diamond (PCD) cladding that coats and hermetically seals the entire individual electrode except for at least a portion of the contact pad and a portion at the second end of the fiber core, wherein the second end of the PCD-cladded BDD fiber core is configured to be inserted between neurons in a brain or within a single neuron in a brain.

In one aspect, the electrode is an electrode having one individual electrode, an electrode comb having at least two of the individual electrodes arranged in a line, or an electrode array having at least three of the individual electrodes arranged in a three-dimensional pattern.

In various aspects, the current technology also provides a method for fabricating an electrode, the method including depositing a first layer of polycrystalline diamond (PCD) onto a substrate; depositing a layer of boron-doped polycrystalline diamond (BDD) on the first layer of PCD; forming the first layer of PCD and the layer of BDD into a pattern, the pattern including a first section defining a contact pad and a second section extending longitudinally from the first section from a first end to an opposing second end that defines an electrode fiber; depositing a second layer of PCD over the entire layer of BDD, except for a portion of the first section and optionally a portion of the second section at the second end, wherein the second layer of PCD contacts the first layer of PCD and hermetically seals the layer of BDD to form the electrode; and removing the electrode from the substrate.

In one aspect, the forming the first layer of PCD and the layer of BDD into a pattern includes forming a hard mask in a shape of the pattern on the layer of BDD and etching the layer of BDD and the first layer of PCD to define the pattern shape.

In one aspect, the depositing a second layer of PCD over the entire layer of BDD, except for a portion of the first section and optionally a portion of the second section at the second end includes depositing a layer of sacrificial photoresist over the layer of BDD and patterning the layer of sacrificial photoresist to expose a portion of the first section and a portion at the second section at the second end; depositing a hard mask over exposed substrate, BDD, and sacrificial photoresist; removing a portion of the hard mask that is deposited on the sacrificial photoresist by dissolving the sacrificial photoresist; depositing the second layer of PCD on areas where there is no hard mask to selectively encapsulate the layer of BDD; and removing the remaining hard mask to yield the electrode coupled to the substrate by way of the first layer of PCD.

In one aspect, the depositing the first layer of polycrystalline diamond (PCD) onto the substrate and the depositing the layer of boron-doped polycrystalline diamond (BDD) on the first layer of PCD are performed by microwave plasma-assisted chemical vapor deposition (MWPACVD), hot-filament chemical vapor deposition (HF-CVD), or a combination thereof.

In one aspect, the method further includes depositing the second layer of PCD over the entire layer of BDD, except for only the portion of the first section, and after the removing, exposing the BDD at the second end of the electrode fiber.

In one aspect, the method further includes integrating the electrode into either a two-dimensional electrode comb or a three-dimensional electrode array.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3A is an illustration of a one-dimensional electrode according to various aspects of the current technology.

FIG. 3B is an illustration of a first two-dimensional fiber comb according to various aspects of the current technology.

FIG. 3C is an illustration of a second two-dimensional fiber comb according to various aspects of the current technology.

FIG. 3D is an illustration of a three-dimensional fiber array according to various aspects of the current technology.

The left column provides a three-dimensional view and the right column provides a cross-section view. The process includes: (i) depositing PCD/BDD on a silicon wafer; (ii) patterning diamond with a copper mask; (iii) depositing and patterning tungsten; (iv) depositing PCD; (v) removing tungsten; and (vi) removing silicon to release a diamond fiber.

Figure 12A:
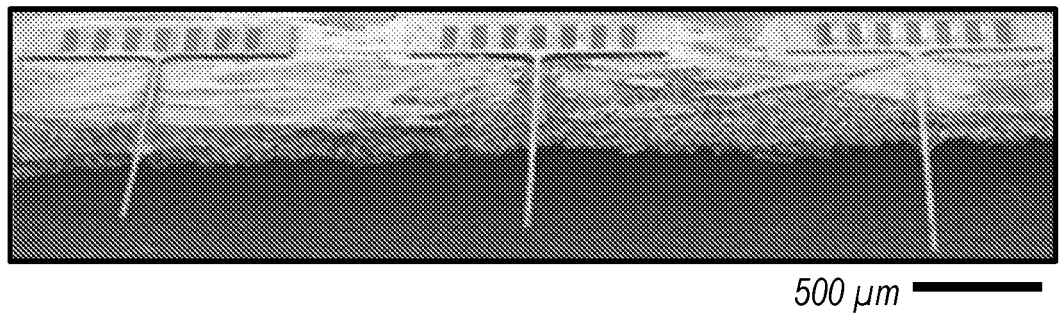

FIG. 12A is a scanning electron microscopy image of a microfabricated, exemplary all diamond microfiber array.

Figure 12B:
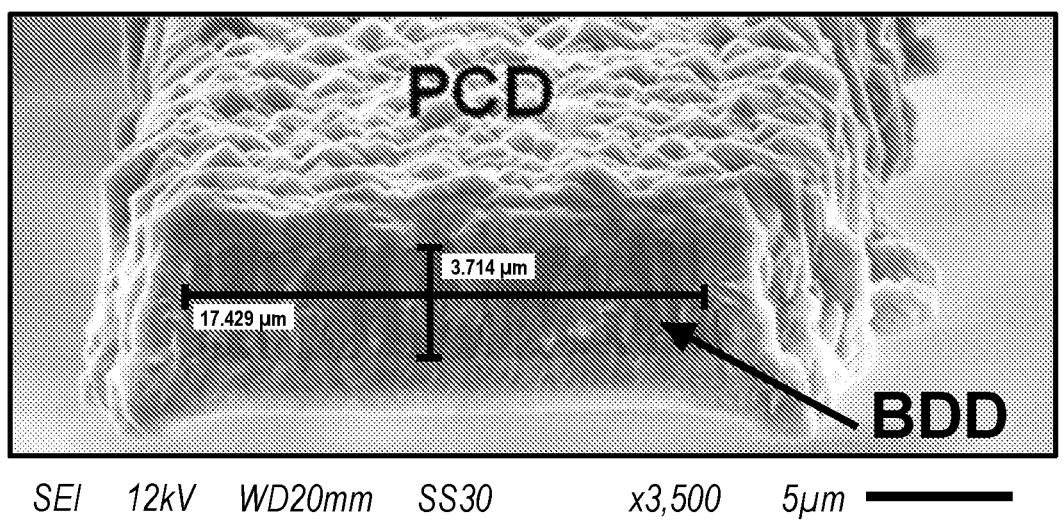

FIG. 12B is a scanning electron microscopy (SEM) image showing a cross-sectional view of an exemplary microfiber having a boron-doped polycrystalline diamond (BDD) core and a polycrystalline diamond (PCD) coating. The BDD core is approximately 17.4 µm wide and approximately 3.7 µm thick. The BDD shows a darker color than PCD under SEM due to its higher electrical conductivity.

Figure 13A:
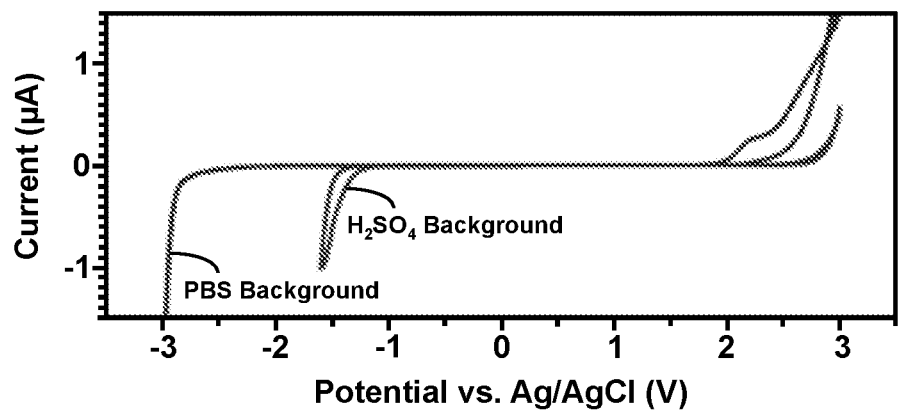

FIG. 13A shows potential window curves of an exemplary diamond fiber electrode measured in PBS buffer pH 7.4 and $H_2SO_4$.

Figure 13B:
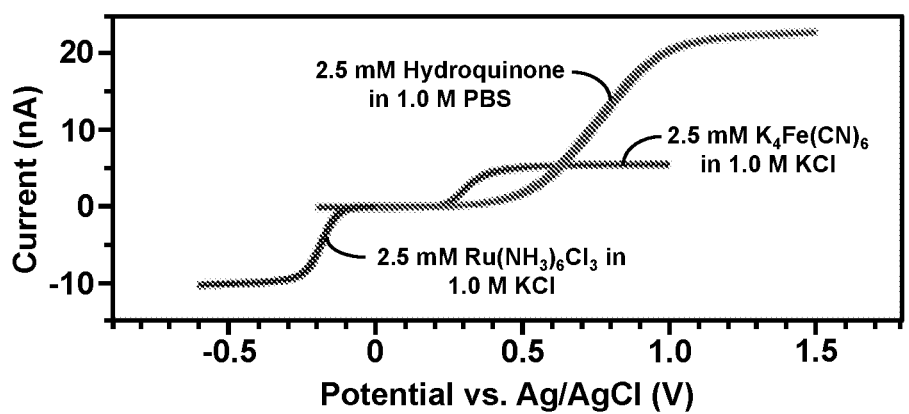

FIG. 13B shows CVs of the exemplary diamond fiber measured in three redox couples.

Figure 13C:
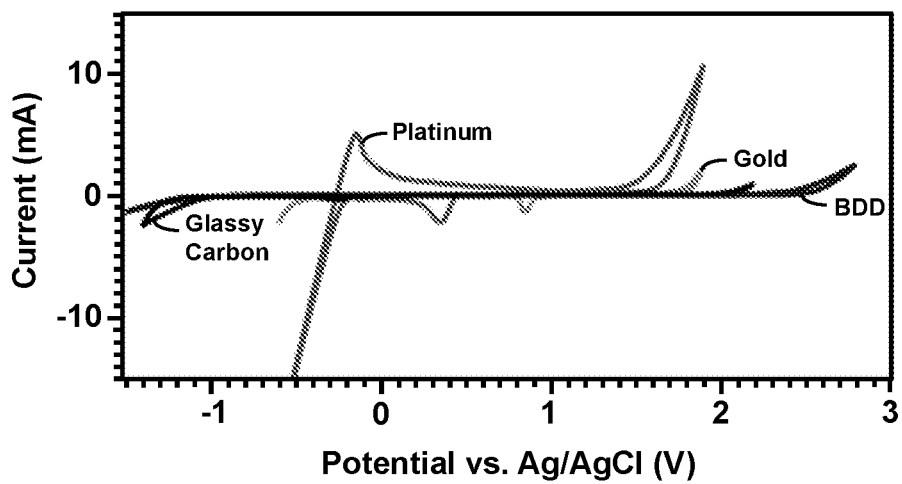

FIG. 13C shows potential window curves for various electrode materials.

Figure 14A:
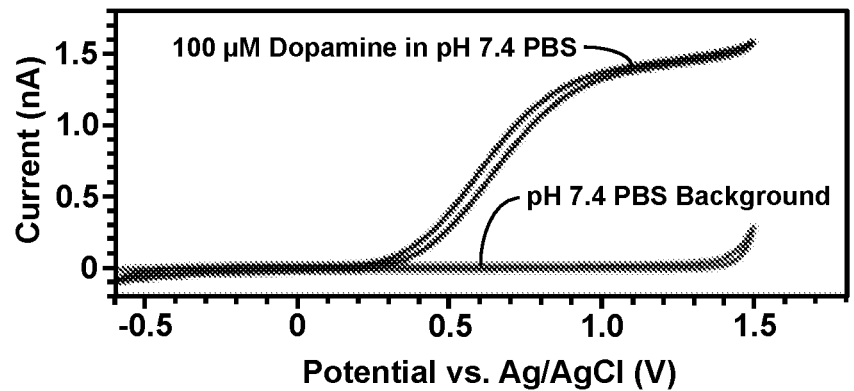

FIG. 14A shows CVs for 0.1 mM dopamine (DA) and phosphate buffered saline (background) scanned at 1.0 V/s.

Figure 14B:
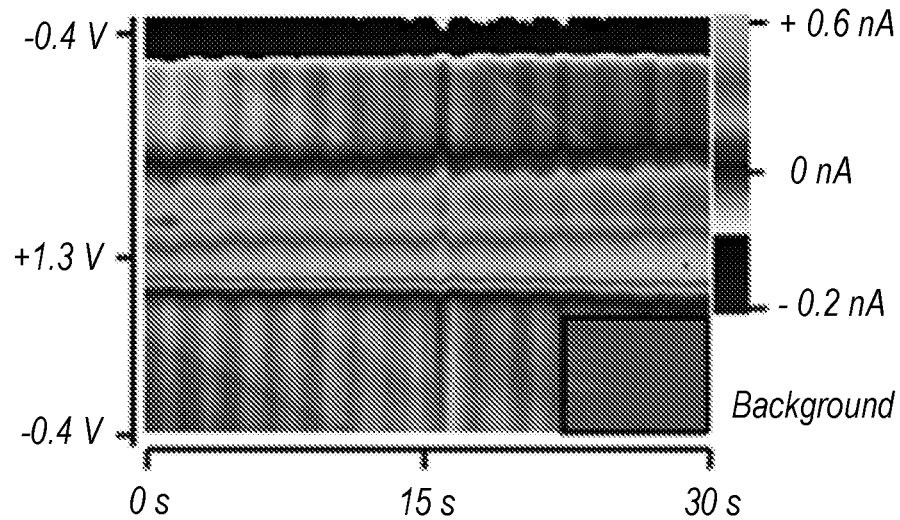

FIG. 14B is a color plot of dopamine (DA) fast-scan cyclic voltammogram (FSCV).

Figure 14C:
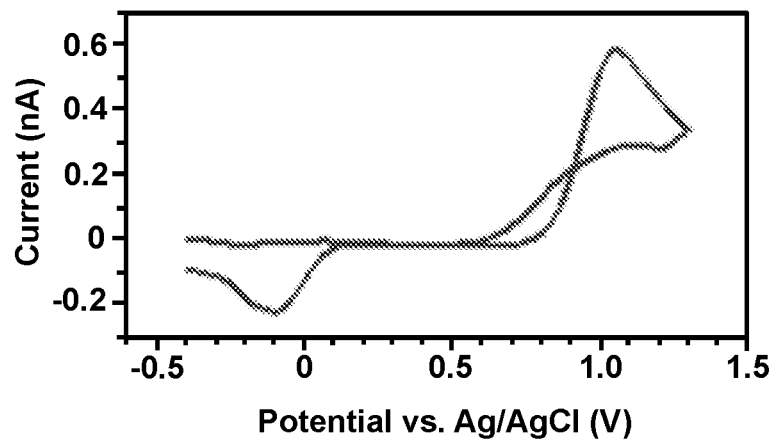

FIG. 14C shows an individual FSCV of DA in phosphate buffered saline pH 7.4. FSCVs of DA are completed in a stagnant electrochemical cell with a scan rate of 400 V/s, a Ag/AgCl reference electrode, and 20 µM DA.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and B.

Example embodiments will now be described more fully with reference to the accompanying drawings.

The current technology provides a revolutionary, all diamond microelectrode configuration that comprises a conductive boron-doped polycrystalline diamond (BDD) fiber core as neural recording electrode and an insulating polycrystalline diamond (PCD) cladding as dielectric barrier and hermetic package. A wafer-scale microfabrication method is developed to construct single- and multi-shank all diamond microelectrode probes. This technique, taking advantages of high-quality diamond materials, makes possible minimally invasive, highly sensitive, and selective neural interface devices useful as long-lasting implants.

Figure 1A:
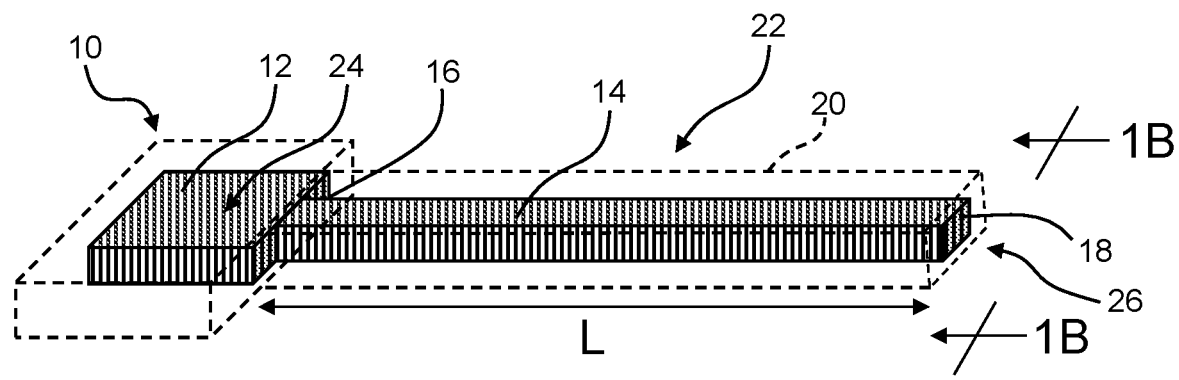
FIG. 1A is an illustration of an electrode according to various aspects of the current technology.

With reference to FIG. 1A, the current technology provides an electrode 10. The electrode 10 comprises a contact pad 12 and a fiber core 14. The fiber core 14 extends longitudinally from the contact pad 12 from a first end 16 that is in direct contact with the contact pad 12 to an opposing second end 18. It is understood that the second end 18 of the fiber core 14 is equivalent to the end of the electrode 10. The contact pad 12 is configured to transfer an electrical signal to a lead and can be any shape that permits such a transfer. In various embodiments, the contact pad 12 has the shape of a rectangle, a square, a triangle, a polygon, a circle, or an oval, as non-limiting examples. Moreover, the contact pad 12 may include at least one aperture (or hole) that facilitates releasing the electrode 10 from a substrate during manufacture and that promotes adhesion of the contact pad 12 to various surfaces as discussed further below (see, for example, FIG. 6A). The contact pad 12 and the fiber core 14 comprise boron-doped polycrystalline diamond (BDD). In some embodiments, the contact pad 12 and the fiber core 14 consist essentially of BDD. BDD exhibits a unique combination of properties that make it a suitable material for biological and chemical sensing and implantable neural stimulation and recording devices. These properties include a high thermal conductivity, a low background current response, a large electrochemical potential window in aqueous solutions, chemical inertness, a high resistance to surface fouling, and biocompatibility.

As used herein, when an electrode component consists essentially of a material, the term "consists essentially of" means that an electrode component includes no other material at levels that positively or beneficially enhance the properties of the material that make the material useful as a material for a specific electrode component. Also, where an electrode component "consists essentially of a material," the component may include trace levels of other contaminating materials, i.e., less than or equal to about 10 wt. %, less than or equal to about 5 wt. %, or less than or equal to about 1 wt. %.

The electrode 10 also comprises an insulating cladding 20 that coats and hermetically seals the contact pad 12 and the fiber core 14. Collectively, the fiber core 14 and the insulating cladding 20 define a shank 22, which shares the first and second ends 16, 18. The insulating cladding 20 comprises polycrystalline diamond (PCD). In some embodiments, the insulating cladding 20 consists essentially of PCD. PCD comprises small grains that range from nanometers to micrometers in size. Accordingly, the PCD can be nanocrystalline diamond (NCD), microcrystalline diamond (MCD), or a combination thereof. The insulating cladding 20 is a continuous layer that is non-porous and free of pinholes or that is substantially free of pinholes (see FIGS. 10A and 10B). As used herein, the term "substantially free" means that a small fraction of the insulating cladding 20 may include pinholes, such as, less than or equal to about 15%, less than or equal to about 10%, less than or equal to about 5%, or less than or equal to about 2.5%. Pinholes are a small holes having an average diameter of greater than or equal to about 10 nm to less than or equal to about 100 nm that potentially cause secondary electrochemical responses that increase background and lower signal to noise ratios (SNRs). Only a first portion 24 of the contact pad 12 and a second portion 26 at or near the second end 18 of the shank 22 are not coated and hermetically sealed by the PCD cladding. The second portion 26 of the second end 18 allows for detection of analytes within a sample, and the first portion 24 of the contact pad 12 allows for the transfer of signal to a lead. As used herein the term "at or near the second end" means that the portion contacts the second end 18 of the shank 22 or is near, i.e., within about 2 mm, within about 1.5 mm, or within about 1 mm, the second end 18 of the shank 22. In FIG. 1A, the second portion 26 is at the second end 18 of the shank 22, which is flat or blunt.

The shank 22 has a length L, measured from the first end 16 to the opposing second end 18, of greater than or equal to about 0.5 mm to less than or equal to about 20 mm, greater than or equal to about 0.5 mm to less than or equal to about 15 mm, greater than or equal to about 0.5 mm to less than or equal to about 10 mm, greater than or equal to about 0.5 mm to less than or equal to about 8 mm, or greater than or equal to about 0.5 mm to less than or equal to about 6 mm. The shank 22 can have a predetermined length depending on how deep the shank 22 is intended to penetrate into a sample, such as a mammalian (including human) or non-mammalian brain.

In some embodiments (not shown), a single electrode of the current technology includes a plurality of fiber cores that are electrically coupled to a corresponding plurality of contact pads. Each of the plurality of fiber cores independently has a length L. However, the plurality of fiber cores are separated from each other and combined into a single shank. Similar to a Michigan-type electrode, each of the plurality of fiber cores is exposed, i.e., not coated by the insulating cladding, along the shank so that multiple measurements can be taken along a single electrode. In such an electrode, the probe shank will have a width $W_{shank}$ of less than or equal to about 500 µm.

Within the shank 22, the fiber core 14 has a rectangular or square cross-sectional shape, with some imperfections in shape being permissible. The cross-sectional shape of the fiber core 14 can be seen in FIG. 1B, which shows the second end 18 of the fiber core 14. The fiber core 14 has a width $W_{Core}$ of greater than or equal to about 0.1 µm to less than or equal to about 25 µm, greater than or equal to about 0.1 µm to less than or equal to about 15 µm, or greater than or equal to about 0.1 µm to less than or equal to about 10 µm and a height $H_{Core}$ of greater than or equal to about 0.25 µm to less than or equal to about 10 µm, greater than or equal to about 0.25 µm to less than or equal to about 7.5 µm, or greater than or equal to about 0.25 µm to less than or equal to about 5 µm. As such, the fiber core 14 has a surface area at the second end 18 of greater than or equal to about 0.025 µm² to less than or equal to about 250 µm². The insulating cladding 20 has a thickness $T_{Clad}$ orthogonal to the fiber core 14 in any direction of greater than or equal to about 0.1 µm to less than or equal to about 10 µm, greater than or equal to about 0.1 µm to less than or equal to about 7.5 µm, or greater than or equal to about 0.1 µm to less than or equal to about 5 µm. Accordingly, the shank 22 has a width $W_{Shank}$ of greater than or equal to about 0.3 µm to less than or equal to about 45 µm and a height $H_{Shank}$ of greater than or equal to about 0.45 µm to less than or equal to about 30 µm. A soma of a human neuron has an average diameter of greater than or equal to about 4 µm to less than or equal to about 100 µm. Therefore, depending on the size of the shank 22, the electrode 10 can be inserted into extracellular space between neurons or within a single neuron soma.

Figure 1B:
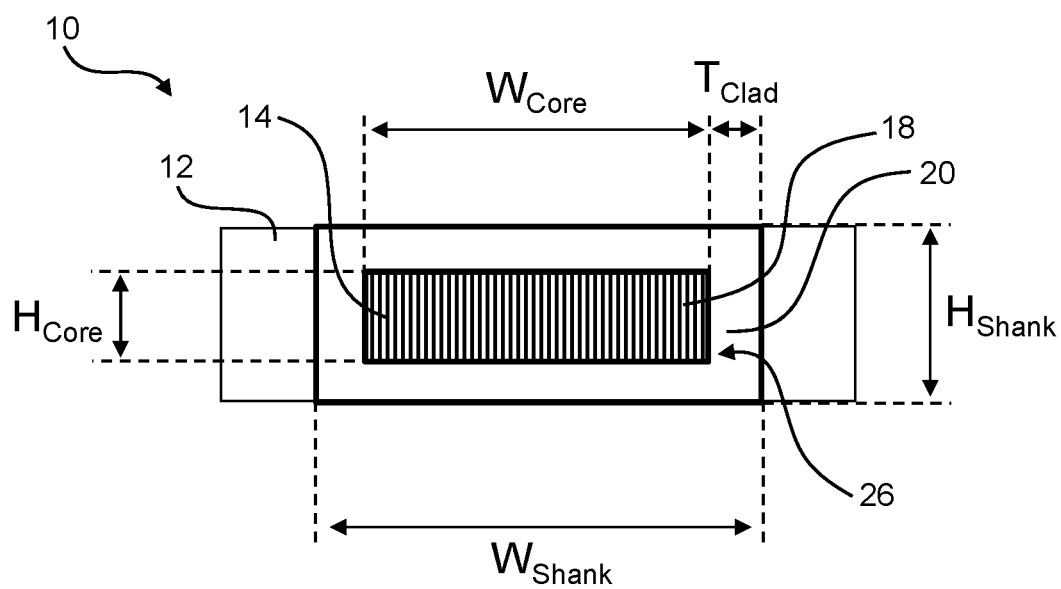
FIG. 1B is a perspective view of the electrode according to FIG. 1A taken along plane 1B.
Figure 2A:
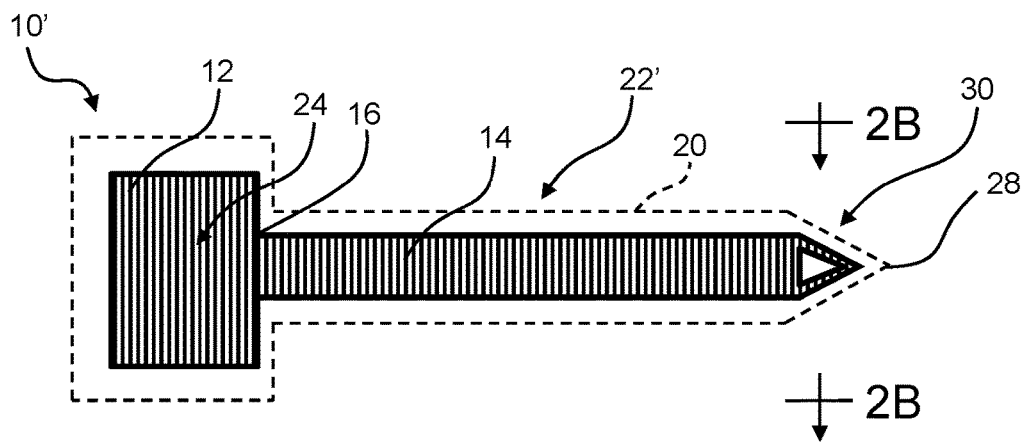
FIG. 2A is an illustration of an electrode according to various aspects of the current technology.
Figures 2B, 2C:
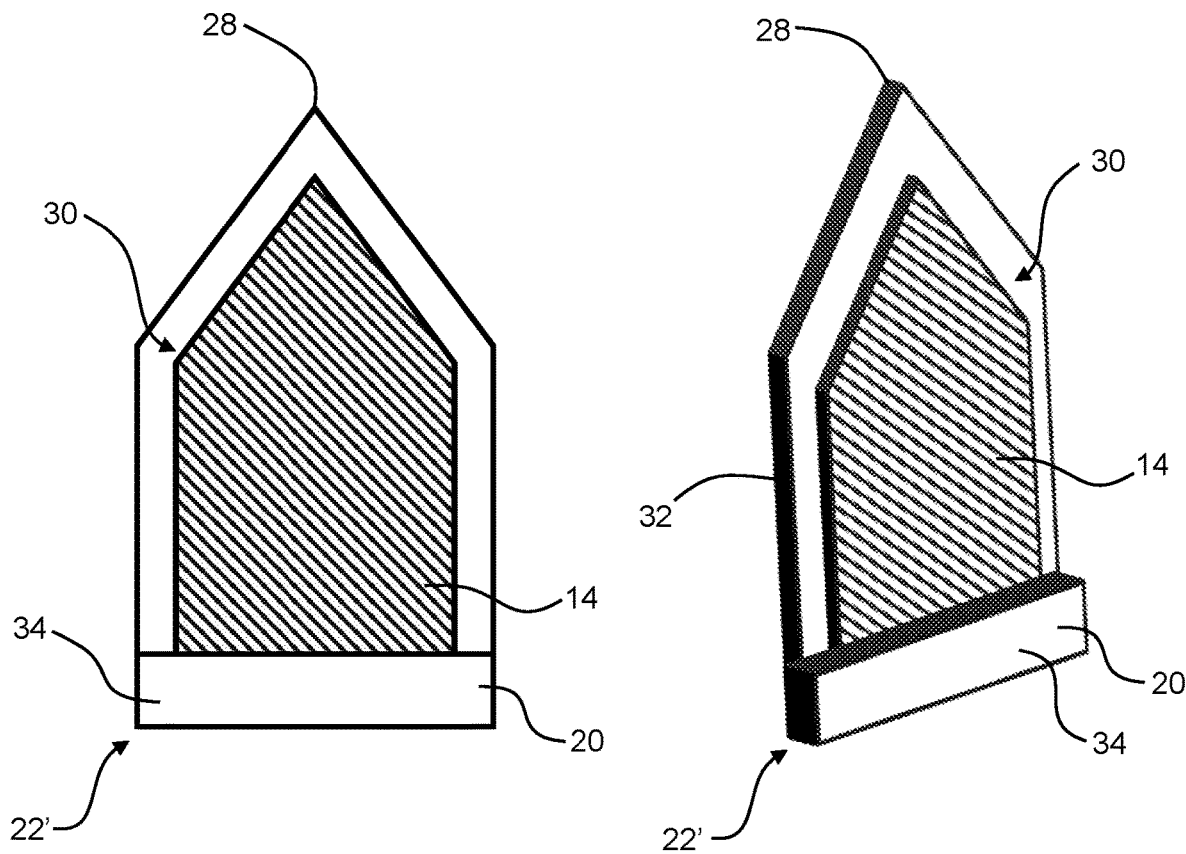
FIG. 2B is a perspective view of the electrode according to FIG. 2A taken along plane 2B.
FIG. 2C is a perspective view of the electrode according to FIG. 2B.

As shown in FIGS. 1A and 1B, the second end 18 of the shank 22 can be flat or blunt. In some embodiments, however, the second end 18 of the shank 22 is pointed and/or sharp. FIG. 2A shows an electrode 10', which has features that correspond to the electrode 10 of FIG. 1A. However, the electrode 10' has a shank 22' having a pointed second end 28. The pointed second end 28 can be sharp or dull (i.e., a rounded point). The fiber core 14 is also pointed, but does not necessarily extend to the second pointed end 28. FIG. 2B is a perspective view of the second pointed end 28 of the shank 22' taken along plane 2B. FIG. 2C is a three-dimensional perspective view of the second pointed end 28 of the shank 22' shown in FIG. 2B. If a cross section was to be taken along the shank 22', it would look like the second end portion 26 of the electrode 10 shown in FIG. 1B. Nonetheless, here a second end portion 30 of the fiber core 14 is disposed on a layer of the insulating cladding 20. However, the insulating cladding 20 does not coat the fiber core 14 at the second end portion 30. The shank 22 comprises a first major longitudinal surface 32 and an opposing second major longitudinal surface 34 and a portion of the second major longitudinal surface 34 is absent at the second end portion 30 of the fiber core 14, such that the fiber core 14 is exposed. Put another way, the second end portion 30 at or near the pointed second end of the fiber core 14 that is not coated and hermetically sealed by the PCD insulating cladding 20 is a longitudinal surface at or near the pointed second end 28 of the fiber core 14, such that the BDD fiber core 14 is exposed at the longitudinal surface at or near the pointed second end 28 of the fiber core 14. The exposed fiber core 14 has a larger surface area than the exposed fiber core 14 of the electrode 10 in FIGS. 1A and 1B. The surface area of the exposed fiber core 14 is greater than or equal to about 1 µm² to less than or equal to about 400 µm², greater than or equal to about 1 µm² to less than or equal to about 350 µm², or greater than or equal to about 1 µm² to less than or equal to about 300 µm².

The electrode 10 of FIG. 1A and the electrode 10' of FIG. 2A can be modified by coating the exposed fiber core 14 at the second end 18, 28 with an adjunct composition that enhances the electrodes' selectivity for specific analytes. As non-limiting examples, the exposed fiber core 14 can be coated with an adjunct composition selected from the group consisting of a sulfonated tetrafluorethylene based fluoropolymer-copolymer (e.g., Nafion), poly(3,4-ethylenedioxythiophene) polystyrene sulfonate (PEDOT:PSS), ozone, and combinations thereof as non-limiting examples.

The electrodes 10, 10' are characterized by an electrochemical impedance at 1 kHz of greater than 0 MΩ, but less than or equal to about 1.5 MΩ, less than or equal to about 1.3 MΩ, less than or equal to about 1.0 MΩ, less than or equal to about 750 kΩ, less than or equal to about 500 kΩ, or less than or equal to about 250 kW. Moreover, the electrodes 10, 10' have a dopamine detection limit of greater than or equal to about 50 nM, greater than or equal to about 40 nM, greater than or equal to about 30 nM, or greater than or equal to about 25 nM.

The electrode 10 of FIG. 1A and the electrode 10' of FIG. 2A can also be modified so that a signal can be recorded from the electrode 10, 10'. An electrode 40 is shown in FIG. 3A in a one-dimensional (1-D) configuration. Here, the electrode 40 comprises a shank 42 of length L and a contact pad 44 as described above. The electrode 40 also has an end portion 46 that can be in accordance with either FIG. 1B or 2B. The electrode 40 is electrically coupled to a flexible ribbon cable 48 by way of a contact 50. The flexible ribbon cable 48 is coupled to a device having a processor.

In some embodiments, at least two electrodes 40 are coupled together and arranged in a line to form a fiber comb. FIG. 3B shows a fiber comb 60 comprising a plurality of electrodes 40 in a two-dimensional (2-D) configuration, i.e., arranged in a line. Each electrode 40 of the plurality independently has an end portion 46 that is blunt (see FIG. 1B) or pointed (see FIG. 2B). Also, each electrode 40 of the plurality independently has a shank 42 having a length L. As shown in FIG. 3B, each electrode 40 has about the same length L. FIG. 3C shows another fiber comb 60', which is the same as the fiber comb 60 of FIG. 3B. However, the fiber comb 60' of FIG. 3C has shanks 42 of different lengths L. In some embodiments, the electrodes 40 are coupled together in order to define the fiber combs 60, 60'. In other embodiments, the electrodes 40 are manufactured simultaneously such that the contact pads 44 are electrically isolated from each other by way of a continuous isolating cladding (not shown) and the electrodes 40 define a single monolithic unit. The shanks 42 of the fiber combs 60, 60' are electrically coupled to the flexible ribbon cable 48 by way of the contact pads 44 and contacts 50. The flexible ribbon cable 48 is coupled to a device having a processor.

In other embodiments, at least three electrodes 40 of FIG. 3A are coupled together and arranged into a fiber array. FIG. 3D shows a fiber array 70 comprising at least three electrodes 40 arranged in a three-dimensional (3-D) pattern or configuration on a circuit substrate 72, such as, for example, a silicon (Si) circuit substrate. Each of the at least three electrodes 40 has an end portion 46 that is blunt (see FIG. 1B) or pointed (see FIG. 2B). Also, each electrode 40 of the plurality independently has a shank 42 having a length L. In FIG. 3D, the shanks 42 independently have varying lengths L as if the four fiber combs 60' of FIG. 3C were disposed onto substrate. However, the current technology provides for any configuration of shank lengths L. In the fiber array 70, each electrode 40 of the plurality is electrically coupled to the circuit substrate 72 by way of contact pads 44 and contacts 74, such as, for example, gold spring contacts, platinum spring contacts, silver spring contacts, copper spring contacts, or spring contacts composed of another electrically conductive metal. Each contact 74 is independently electrically coupled to a flexible ribbon cable 76 by way of leads 78 and a connector 80 (see the exploded view in FIG. 3D). The flexible ribbon cable 76 is coupled to a device having a processor. In some embodiments, the electrodes 40 are coupled together in order to define the fiber array 70. In other embodiments, each row of the electrodes 40 are manufactured simultaneously such that the contact pads 44 are electrically isolated from each other by way of a continuous isolating cladding (not shown) and the electrodes 40 define a single monolithic row. A plurality of rows can be electrically coupled to the circuit substrate 72 to define the fiber array 70.

The current technology further provides a method for fabricating an electrode. The electrode can be any electrode or combination of electrodes described above. The method comprises depositing a first layer of PCD onto a substrate. The substrate can be, for example, a silicon (Si) wafer, a silicon dioxide (silica or $SiO_2$) wafer, or a Si wafer having silica-modified surface.

The method then comprises depositing a layer of BDD onto the first layer of PCD. The depositing the first layer of PCD onto a substrate and the depositing the layer of BDD on the first layer of PCD are performed by microwave plasma-assisted chemical vapor deposition (MWPACVD), hot-filament chemical vapor deposition (HF-CVD), or a combination thereof.

The method then includes forming the first layer and the second layer into a pattern. The pattern comprises a first section that defines a contact pad and a second section extending longitudinally from the first section from a first end to an opposing second end that defines a fiber core. In various embodiments, the forming the first layer and second layer into a pattern comprises forming a hard mask in a shape of the pattern on the layer of BDD and etching the layer of BDD and the layer of PCD to define the pattern shape.

The method also comprises depositing a second layer of PCD over the entire layer of BDD except for a portion of the first section and optionally a portion of the second section at or near the second end. The second layer of PCD contacts the first layer of PCD and hermetically seals the layer of BDD to form the electrode. In various embodiments, the depositing a second layer of PCD over the entire layer of BDD except for a portion of the first section and a portion of the second section at the second end comprises depositing a layer of sacrificial photoresist over the layer of BDD and patterning the layer of sacrificial photoresist to expose a portion of the first section and a portion at the second section at the second end; depositing a hard mask comprising tungsten or copper as non-limiting examples over a exposed substrate, BDD, and the sacrificial photoresist; removing a portion of the hard mask that is deposited on the sacrificial photoresist by dissolving the sacrificial photoresist in acetone and rinsing in isopropyl alcohol and deionized water; depositing the second layer of PCD by MWPACVD or HF-CVD on areas where there is no hard mask to selectively encapsulate the layer of BDD; and removing the remaining hard mask to yield the electrode coupled to the substrate by way of the first layer of PCD.

The method then comprises removing the electrode from the substrate. In various embodiments, the removing the electrode from the substrate comprises deep silicon dry etching the substrate. Where the second layer of PCD covers and hermetically seals the BDD at the second section, a portion of the second end of the fiber core is removed to expose the BDD. Removing a portion of the second end is performed by plasma etching, laser cutting, cutting with a blade, or hand cleavage. The exposed BDD is suitable for electrophysiology recording and chemical sensing.

Embodiments of the present technology are further illustrated through the following non-limiting examples.

Example 1

Technical Description.
Device Design.

The current technology provides a design and fabrication method of all diamond microelectrodes capable of monitoring extracellular biopotentials and chemical signals of neurons with high spatiotemporal resolution, excellent long-term stability, and minimal invasiveness.

The diamond microfiber electrode comprises a conductive boron-doped polycrystalline diamond (BDD) microfiber core and an insulating polycrystalline diamond (PCD) cladding. The BDD core is used to record neural biopotentials and neurotransmitter signals in the nervous systems, such as the brain and peripheral nerves, while the PCD cladding serves as a dielectric barrier and hermetic package to prevent signal cross-talking and device corrosion.

Figure 4:
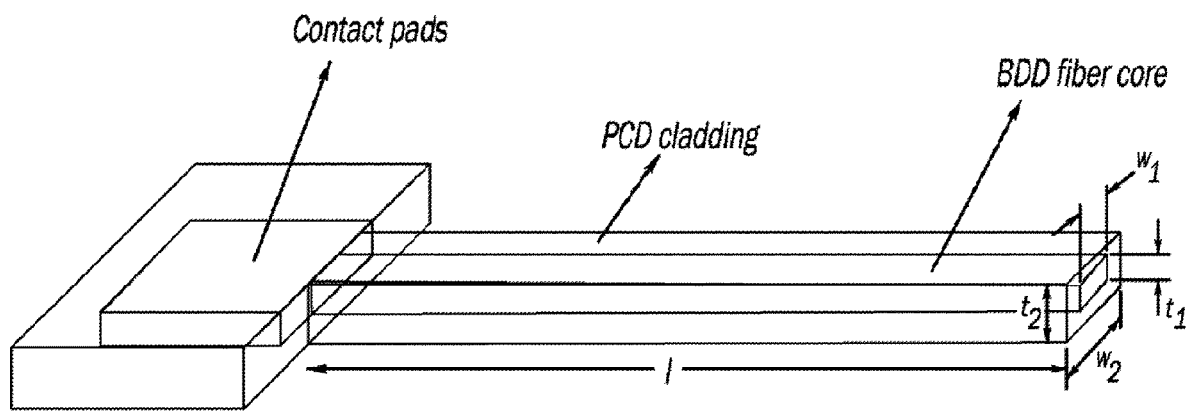
FIG. 4 is an illustration of an exemplary electrode made according to various aspects of the current technology.

A diagram of the diamond electrode is illustrated in FIG. 4. The microfiber has an overall length (l) of 3-5 mm in order to target neurons in deep brain regions of, for example, rodents. However, longer microfibers can be included in order to reach deep brain regions of other animals, such as, for example, humans. The BDD fiber core has a rectangular cross-section with dimensions of 1-25 μm in width ($w_2$) and 0.5-5 μm in thickness ($t_2$), which matches the size of neurons to enable single-unit recording of target cells. The PCD cladding, with a thickness of 0.5-5 μm, covers an individual BDD core conformally as an insulating coating. The microfiber is connected to peripheral recording electronics via a contact pad made out of BDD. With the current novel microfabrication method, the diamond microfiber electrode can be constructed into various configurations: a single electrode probe or an electrode array with multiple single-/varying-length probe shanks. The dimensions of the electrodes can be scaled down to submicron ranges and precisely adjusted based on the user's demand.

Fabrication Method.

Figure 5:
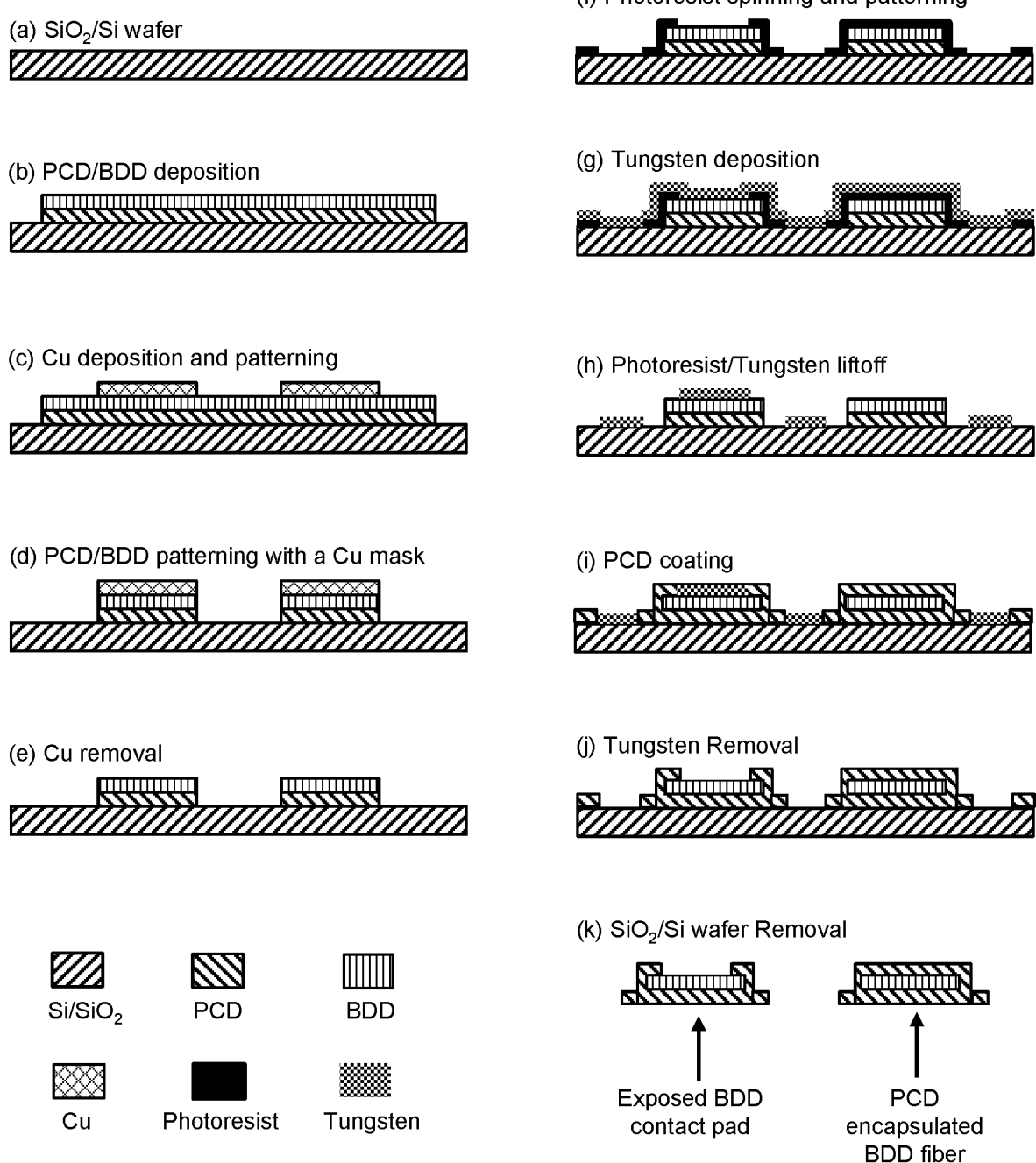
FIG. 5 shows illustrations of a process flow for microfabrication of single- and multi-shank all diamond microelectrodes in accordance with various aspects of the current technology.

A wafer-scale microfabrication method is developed to construct single- and multi-shank, all diamond microelectrodes. FIG. 5 shows a detailed process flow. One micron $SiO_2$ is optionally coated on a Si wafer using plasma enhanced chemical vapor deposition (PECVD) (PlasmaLab 80Plus®, Oxford Instruments) (a). A microcrystalline PCD film is grown using a custom-designed microwave plasma assisted chemical vapor deposition reactor (MWPACVD) (Lambda Technologies, Inc.) with methane gas, followed by BDD growth in MWPACVD with a gas mixture of hydrogen-diborane and methane (b). A metal such as copper (Cu) is thermally evaporated (Edwards Vacuum Coater Auto 306) on top of diamond and patterned using ultraviolet photolithography to form a hardmask for plasma dry etching of diamond films (c). The BDD/PCD multilayer film is plasma etched in a reactive ion etcher (Lambda Technologies, Inc.) using $SF_6/Ar/O_2$ as processing gases to define the electrode shape (d). A layer of sacrificial photoresist is spun and patterned to expose contact pads and areas surrounding the electrode (f). Tungsten (W) is deposited over the pre-patterned photoresist and lifted off by dissolving the sacrificial photoresist in acetone, followed by a thorough rinse in isopropyl alcohol and deionized (DI) water (g and h). Another layer of PCD is grown to selectively encapsulate the BDD areas where there is no tungsten coating (i). After removing tungsten completely by boiling the entire substrate and associated layers in aqua regia (1:3 $HNO_3$:HCl) for greater than or equal to about 10 seconds to less than or equal to about 5 minutes (j), the devices are diced using a laser (Bettonville UltraShape 5XS) and then released from the substrate (k) by etching the Si substrate in a mixture of hydrofluoric acid (HF) and nitric acid ($HNO_3$) solutions ($HF:HNO_3$-50:50 vol. %) at room temperature. If $SiO_2$ is deposited in Step (a), device releasing can be achieved by undercutting the sacrificial $SiO_2$ in buffered HF solution (10% HF). After releasing the device from the substrate, laser cutting, plasma etching, or hand cleavage is used to expose pristine BDD at the fiber tip.

Advantages and Improvements Over Existing Methods, Devices, and Materials.

A unique solution to the above challenges is an all diamond microfiber electrode comprising a conductive BDD core as a recording electrode and an insulating PCD cladding as a dielectric barrier and hermetic package. Compared to $sp^2$ carbon found in conventional carbon fiber materials, the $sp^3$ carbon of BDD enables lower background current and higher signal-to-noise ratio of neural recordings. Furthermore, the low absorption surface of the diamond encapsulation makes the electrode extremely resistant to biofouling and deactivation, enabling long-term reliability and stability of recordings during chronic implantation. Taking advantage of modern lithography techniques (e.g., ultraviolet photolithography and electron-beam lithography), the dimensions of the proposed device are comparable to or even smaller than conventional carbon fiber electrodes, which minimizes the invasiveness of implants. Lastly, the new microfabrication method allows wafer-scale, mass production of the diamond electrodes. This significantly reduces the fabrication complexity, resulting in a time-efficient, less expensive, and scalable process. This technique yields minimally invasive, highly sensitive, and selective neural interface devices and long-lasting implants for fundamental and clinical neuroscience studies and treatments.

Exemplary Electrode.

Figure 6A:
FIG. 6A is a scanning electron microscopy image of an exemplary diamond microfiber core and contact pad.
Figure 6B:
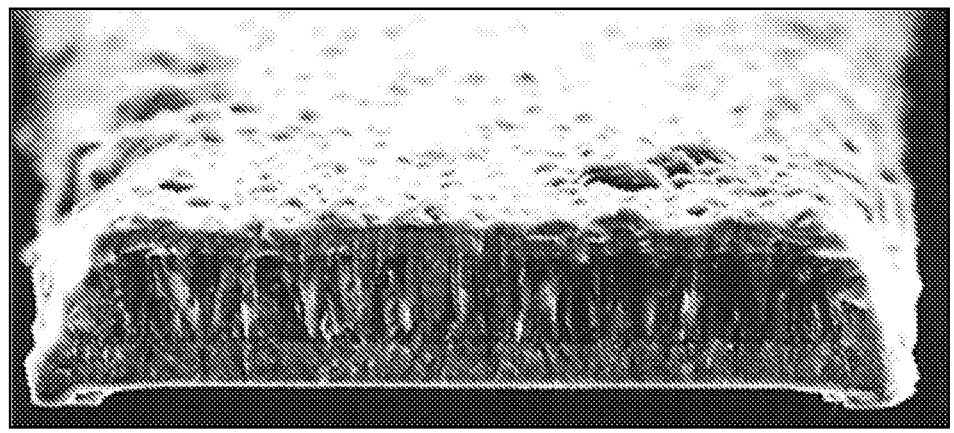
FIG. 6B is a scanning electron microscopy image of a microfiber tip of the microfiber core shown in FIG. 6A.

Here, key microfabrication techniques are developed and the main fabrication steps for electrode devices completed. FIGS. 6A and 6B show scanning electron microscopy (SEM) images of a fabricated exemplary all diamond microfiber electrode. FIG. 6A shows the diamond microfiber and contact pad, while FIG. 6B shows the microfiber tip. A clear distinction between the BDD microfiber core and insulating PCD cladding is visible in FIG. 6B.

Figure 7:
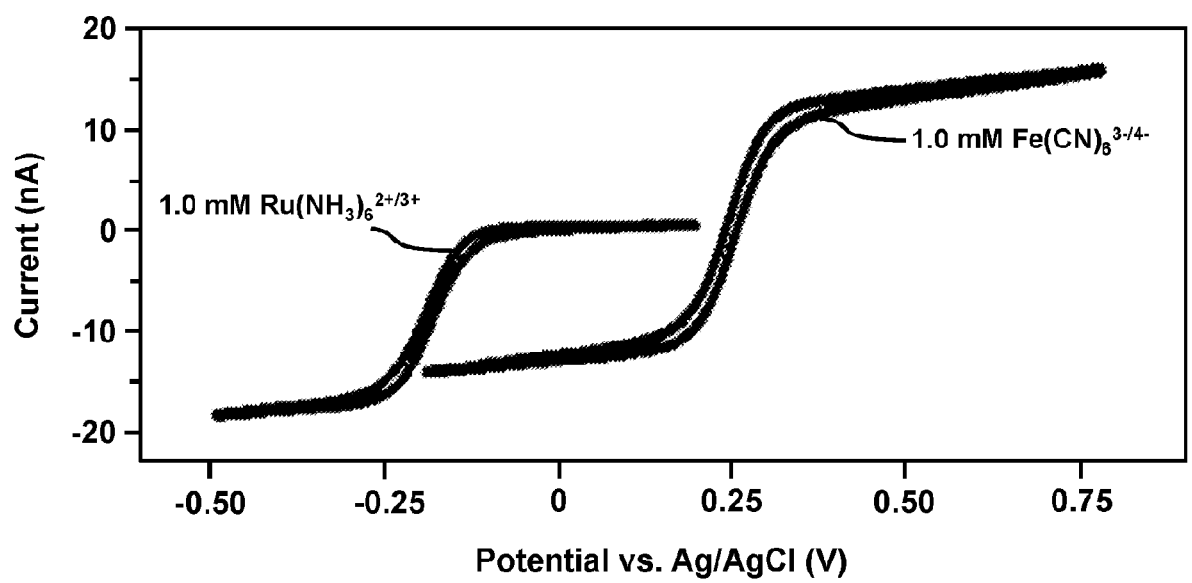
FIG. 7 shows cyclic voltammograms (CVs) generated from an exemplary all diamond microfiber electrode made according to various aspects of the current technology.
Figure 8:
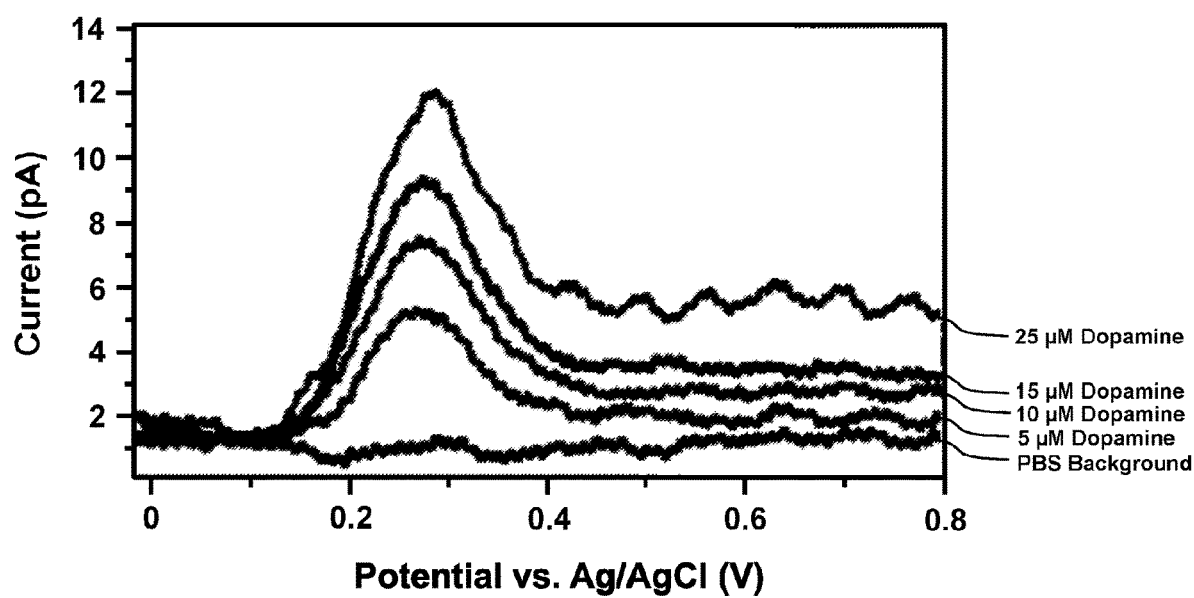
FIG. 8 shows square wave voltammograms generated from an exemplary all diamond microfiber electrode made according to various aspects of the current technology.

Fabricated devices are tested ex vivo using cyclic voltammetry (CV) to study general electrochemical characteristics. For proper electrical connection and mechanical stability for ex vivo testing, the diamond microfibers are mounted on a custom-made PCB stick. Results are illustrated in FIG. 7, which shows CVs of two one-electron transfer redox couples, ferri/ferrocyanide ($Fe(CN)_6^{3-/4-}$), and ruthenium hexamine ($Ru(NH_3)_6^{2+/3+}$). The CVs shown in FIG. 7 exhibit the trademark sigmoidal response characteristic of microelectrodes (radius of the electrode is smaller than that of the diffusion profile of the analyte of interest). The obtained sigmoidal CV shape is especially useful for the $Fe(CN)_6^{3-/1-}$ redox couple as this electron transfer reaction is known to be sensitive to the diamond electrode surface. In addition, the magnitude of the steady-state current responses for the anodic and cathodic scans are nearly identical, indicating a reversible electron transfer process. The SEM micrographs shown in FIGS. 6A and 6B and corresponding CV results in FIG. 7 give clear indication that the BDD microfiber core is completely insulated by the dense PCD cladding. Squarewave voltammetry (SWV) is also conducted to demonstrate the feasibility of ex vivo dopamine sensing using the diamond fiber microelectrodes. Dopamine is serially diluted in phosphate-buffered saline (PBS) solution from 0 µM to 25 µM. As shown in FIG. 8, sharp and well-resolved oxidation peaks in response to different dopamine concentrations demonstrate the efficacy of the diamond fiber for dopamine sensing.

Example 2

Device Geometry Design.

Figure 9:
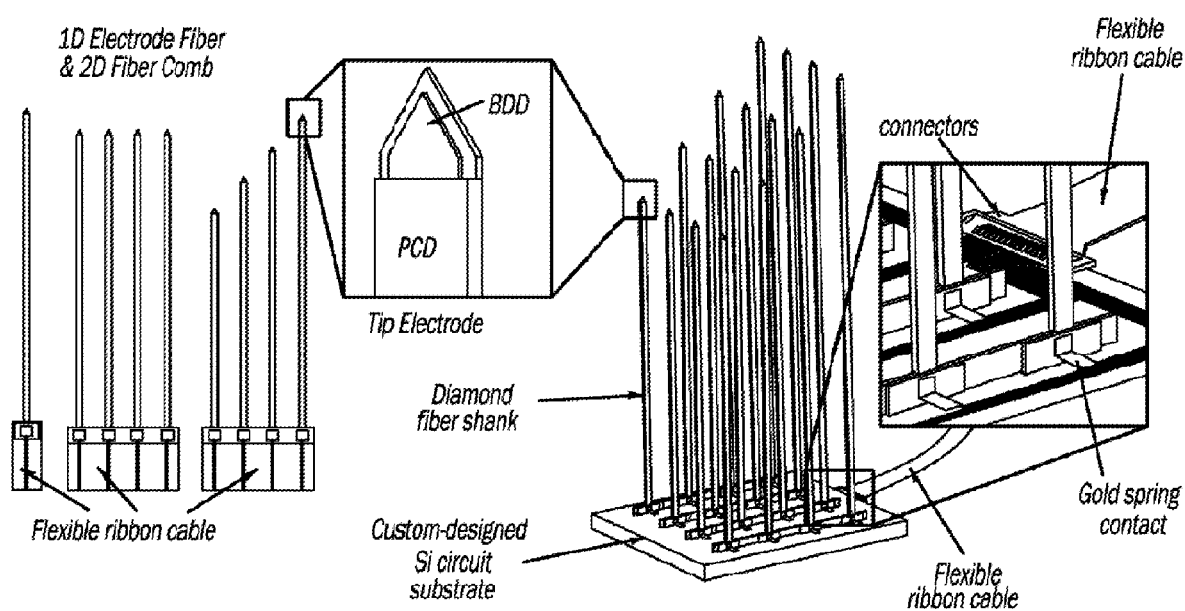
FIG. 9 is a diagram of exemplary diamond ultramicrofiber electrodes in 1D fiber, 2D fiber comb, and 3D array configurations.

As illustrated in FIG. 9, an exemplary novel all diamond fiber described here comprises an ultra-fine boron-doped polycrystalline diamond (BDD) conducting core encapsulated in a thin polycrystalline diamond (PCD) insulating cladding. The BDD core has a rectangular cross-section with widths of 1-20 µm and thicknesses of 0.5-5 µm, resulting in an effective recording area of less than 50 µm². Such electrode dimensions match the size of small soma (only 8-15 µm in diameter), enabling single-unit recording and neurotransmitter sensing from target neurons with cellular resolution and high fidelity. With thicknesses of only 0.5-1 µm, the PCD cladding provides sufficient dielectric strength to prevent signal cross-talking, while serving as a biocompatible, fouling-resistant, and hermetic package for the electrode. The fiber tip is tapered down to submicron scale, which facilitates fiber insertion into brain tissues without disruption of the blood-brain barrier. The diamond electrodes are microfabricated as 1D fibers or 2D fiber combs, combining multiple parallel fibers of equal or varying lengths. Each individual fiber or comb is assembled with a mechanically flexible ribbon cable via large contact pads made out of BDD. High-density 3D fiber arrays are implemented by integrating 2D combs and peripheral electronics onto a custom-designed circuit substrate made out of silicon, similar to those previously reported, and by NeuroNexus. The flexible ribbon cable is connected to standard connectors compatible with most commercial recording and data acquisition instruments. For proof-of-concept devices used in rodents, the fibers have lengths of 3-5 mm to target neurons in the deep brain regions. The distance between the fiber tips (the recording site spacing) can vary from 50-300 µm based on the desired density of recordings. Further improvements in the spatial coverage of probing are achieved by minimizing fiber spacing to optimize the lateral resolution, as well as by integrating varying length fibers on a single array to increase the depth coverage.

Synthesis, Analysis, and Optimization of Insulating and Conductive Diamond Thin Films.

Both microcrystalline diamond (MCD) and nanocrystalline diamond (NCD) morphologies are investigated. Diamond synthesis parameters of the MW-PACVD process, such as pressure, power, temperature, methane to boron ratio, and growth time, are adjusted to optimize diamond quality, doping level, film thickness, and surface adsorption of chemicals and cells. Additionally, undoped PCD films of different crystal granularity (MCD vs. NCD) and thicknesses are grown under various deposition conditions (pressure, power, temperature, and growth time) and investigated to achieve the optimal performances of dielectric strength, chemical barrier properties, and cell biocompatibility.

Figure 10A:
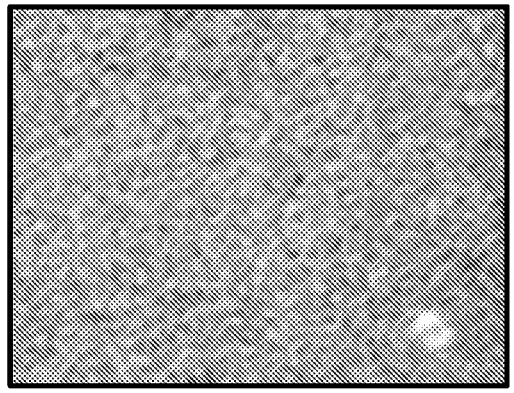
FIG. 10A is a scanning electron microscopy image of an exemplary polycrystalline diamond film that is free of pinholes.
Figure 10B:
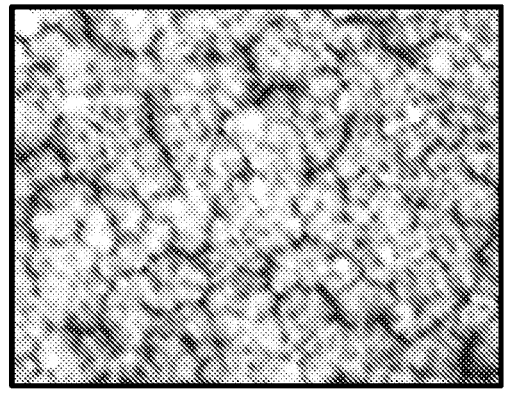
FIG. 10B is a scanning electron microscopy image of an exemplary polycrystalline diamond film having pinholes.
Figure 10C:
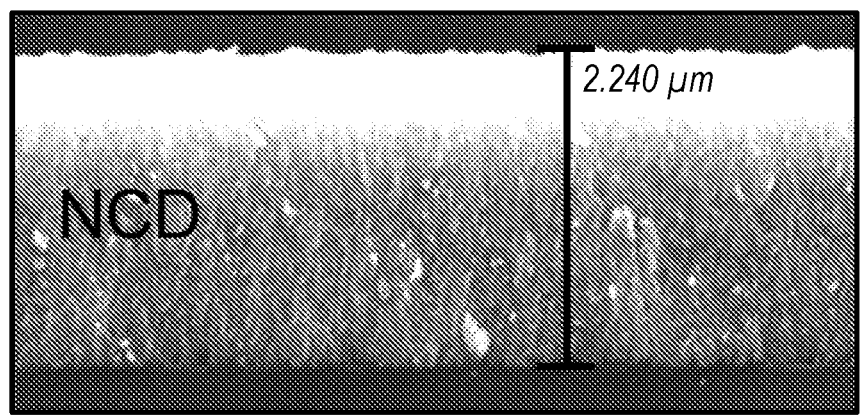
FIG. 10C is a scanning electron microscopy image of an exemplary nanocrystalline diamond film that is free of pinholes.

For MW-PACVD of diamond films, special attention is paid to substrate seeding/diamond nucleation prior to diamond growth. A dense nucleation layer is needed to avoid pinholes originating at the silicon/diamond interface as shown in FIG. 10A. These pinholes, as shown in FIG. 10B, can potentially cause secondary electrochemical response, increasing the background and lowering SNR. A nucleation study is conducted to compare scratch seeding with ultrasonic seeding and ultrasonic seeding in combination with a pretreatment step. Additionally, MCD vs. NCD morphology is compared. The NCD material is grown at a higher re-nucleation rate, resulting in a pinhole-free and denser film at comparable film thicknesses as shown in FIG. 10C. Furthermore, utilizing an NCD film for the enclosure of the conductive diamond core can achieve a much smoother film, allowing better control of the hard mask necessary for the plasma etching process. This not only lowers the risk of cracks, but also allows for the reduction in the overall cross-sectional area of the ultramicrofiber.

Electrochemical analysis includes probing the film's response to dopamine and various standard redox couples, such as ferri/ferrocyanide ($Fe(CN)_6^{-3/-4}$) and ruthenium hexamine ($Ru(NH_3)_6^{+2/+3}$). To study the impact of various levels of oxygen termination on the electrochemical performance of diamond films, oxygen termination is achieved via chemical, electrochemical, ozone, and oxygen plasma treatments. The different treatment options undergo electrochemical dopamine detection, identifying corresponding detection limits and long-term stability. Complementary analytical techniques utilized are water contact angle (WCA) and XPS analysis, revealing the surface character of hydrophobicity, C/O ratio, and C—O functional groups. Boron concentration and diamond quality are estimated by Raman analysis. The boron concentration is verified via secondary ion mass spectroscopy (SIMS). 2-point and 4-point probe and Hall measurements are utilized to quantify electrical resistivity/conductivity. Surface topography, diamond crystal size, and surface roughness are analyzed via SEM and surface profiler. Atomic force microscopy (AFM) and field emission scanning electron microscope (FE-SEM) are used to investigate substrate nucleation densities and the nucleation layer after diamond separation from the substrate. LAwave™, a material and thin film tester based on the dispersion of surface acoustic waves, is used to measure the Young's Modulus of the diamond films. Cultured neuron assays are used to study the effects of diamond morphology and surface chemistry on cell growth, viability, and recording quality ex vivo.

Wafer-Scale Fabrication and Integration of all Diamond Ultramicroelectrode Arrays.

Figure 11:
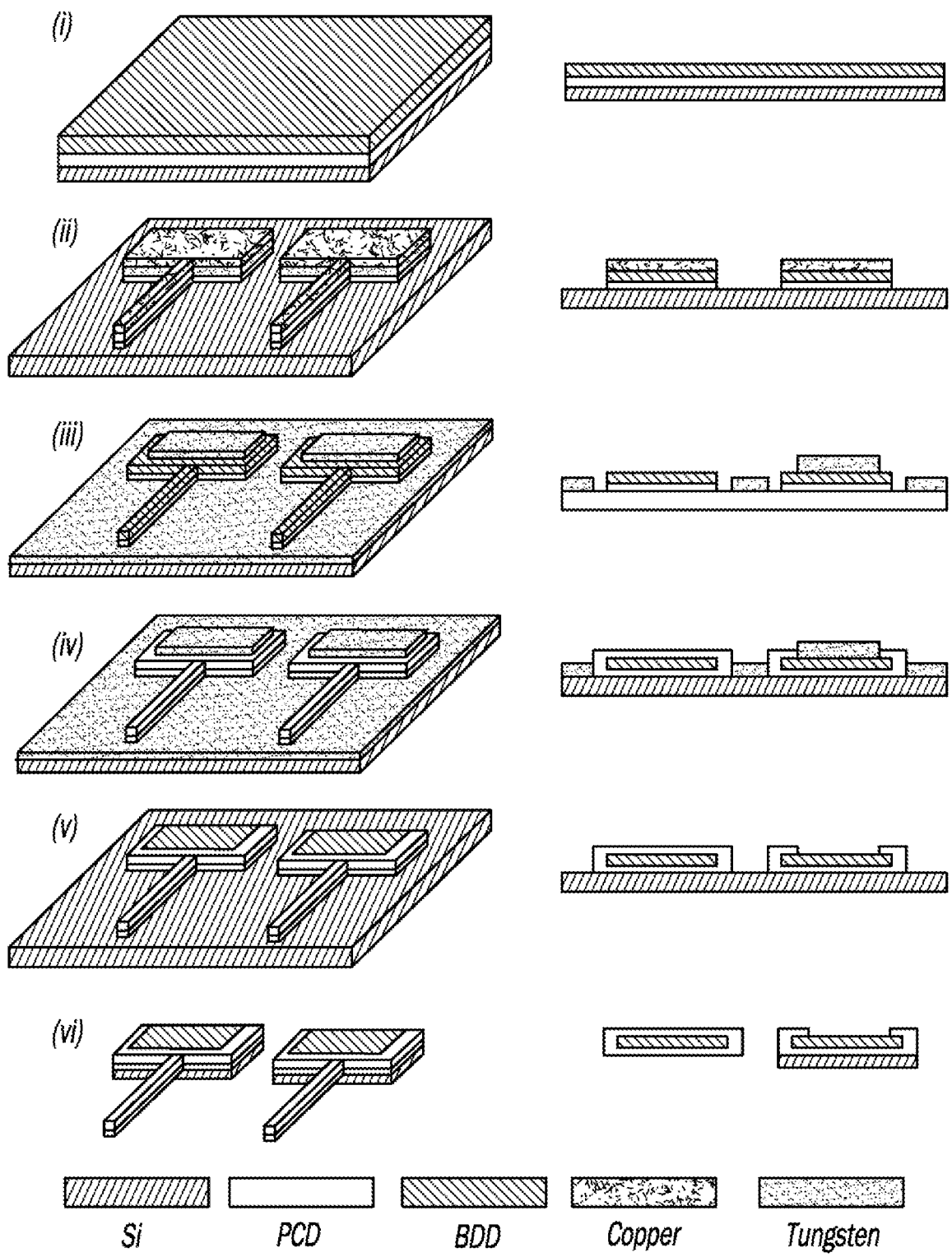
FIG. 11 is an illustration of an exemplary microfabrication process flow.

Wafer-scale, reliable fabrication methods are developed and optimized for mass production of the all diamond ultramicroelectrodes described herein. As illustrated in FIG. 11, thin PCD and BDD films are deposited consecutively on a 4" silicon wafer, using the MW-PACVD method. Copper is thermally evaporated on the BDD surface and chemically etched to form a hard mask for diamond patterning. Sputtered aluminum and plasma enhanced chemical vapor deposited (PECVD) $SiO_2$ can also be used as hard masks, which have been tested to plasma etch diamond materials in previous studies. Hard masks applied onto micro/nanocrystalline BDD films are patterned using well-established microfabrication photolithographic processing techniques. Structuring the grown BDD/PCD films is done by dry plasma etching utilizing a microwave plasma assisted electron cyclotron resonance system with a gas mixture of $SF_6/Ar/O_2$. After removing the hard mask, tungsten is sputtered and selectively patterned to cover the recording tip, central part of contact pads, and space between individual devices. Since diamond growth on tungsten is much slower than that on the BDD, the subsequent PCD deposition covers only the fiber shank as a dielectric barrier, leaving the fiber tip, contact pads, and surrounding areas open. After tungsten removal, deep silicon dry etching is applied to completely remove the silicon substrate from the backside of the fiber shank, while keeping silicon underneath the contact regions as support structures to facilitate the device handling during 3D assembly.

The plasma etching of the combined BDD and PCD film is a key step in determining the fiber dimensions and spatial resolution. Although hard masks made of evaporated copper, sputtered aluminum, and PECVD $SiO_2$ are viable options, some undesirable side effects can occur during plasma etching of diamond. These side effects include: a) partial masking of to-be-etched surfaces due to the particulate transfer of hard mask material during the etch process causing needle forest-like structures to remain on the surface after etching, and b) over-etching of not-to-be-etched surfaces due to mask breakdown. Optimization of the etching process includes adjustment of process parameters, such as pressure, power, substrate bias, and gas chemistry. Dimensions of hard masks can be modified as necessary to compensate for undesired over-etching. Smoother NCD BDD or polished MCD BDD films with the roughness of less than 10 nm can be utilized in order to push the linewidth of structures below 5 μm. Furthermore, using tungsten shadow masks for selective diamond deposition improves the precision of diamond patterning and fabrication efficiency by eliminating plasma etching. Shadow masks made out of other materials (e.g. copper) are studied and compared with tungsten in terms of diamond growth rate and quality.

The novel fabrication method described here is adapted from well-established semiconductor microfabrication techniques, allowing monolithic fabrication of approximately 800 diamond fibers with different geometries on a 4" wafer. The process is scalable up to 6" wafers in order to further reduce the fabrication cost. By taking advantage of UV and electron-beam (e-beam) lithography techniques, the device dimensions can further be miniaturized to the submicron scale. The proposed fabrication technique can also be used to build "Michigan"-style all diamond probes with larger dimensions, where there will be multiple electrode sites on a single shank to maximize the longitudinal density of recordings.

For the integration of fiber arrays, highly flexible ribbon cables are made out of photolithographically patterned gold contact pads and traces on polyimide substrates to form the interconnects between diamond fibers and recording instruments. Single-shank fibers and multi-shank 2D combs are assembled directly to the flex cables using flip-chip bonding with gold pumps. High-density 3D fiber arrays are achieved by integrating multiple 2D combs onto a compact, custom-design silicon circuit substrate as shown in FIG. 9. On the platform, microgrooves that match the size of the electrode backbone are fabricated using deep reactive ion etching or laser cutting. After inserting the comb electrodes into the grooves, out-of-plane interconnects to the electrode pads are made through overhanging gold spring contacts electroplated around the edges of the grooves. The contacted areas are covered with biocompatible epoxy for enhanced mechanical strength and dielectric encapsulation. The connection between the silicon platform and polyimide ribbon cables is achieved through commercial connectors or flip-chip bonding. This assembly approach is selected over other methods to realize a thin backbone required for floating chronic implantation of the arrays. Floating implantation improves recording stability by reducing the destructive forces applied to the brain tissues as a result of mechanical decoupling to the skull.

One scaling bottleneck of high-channel-count arrays is the spatial limitation of interconnects between analog front-ends and electrodes. To address this issue, multiplexing architectures are implemented to allow many electrodes to be accessed using a small number of control and data lines. For the first generation devices, commercial Intan chips with a built-in analog multiplexer (intantech.com) are flip-chip bonded onto the backend of the custom-design silicon platform proposed. An array of electrodes are multiplexed to a single output pin, so that multiple recording channels can share a single A/D converter. The arrays are tethered to external recording instruments through standard Omnetic and/or ZIF connectors.

Microfabrication of all Diamond Fiber Microelectrodes.

Here, all diamond fiber microelectrodes (arrays) are developed, eliminating metal altogether. FIG. 12A shows an example of the microfabricated diamond fiber array and the close-up view of a single fiber electrode after silicon removal. The scanning electron microscope (SEM) image in FIG. 12B gives clear indication that the BDD microfiber core is completely insulated by the dense PCD cladding. These fibers have a rectangular tip with cross-sectional dimensions of tens of microns. Each fiber is connected to a backbone contact pad made out of BDD. To fabricate the diamond fibers, thin MCD and MCD-BDD films are grown consecutively on a Si wafer in the MW-PACVD reactor, followed by plasma dry etching to define the structures of the diamond electrodes and contacts. After that, another MCD layer is grown to selectively encapsulate the BDD fibers, leaving the BDD contact areas exposed. After the fibers are released from the silicon substrate in a mixture of HF and $HNO_3$ (HNA) solutions, the fiber tip is cleaved to expose pristine BDD at a blunt end as a recording site. To form a pointed tip, during the second PCD deposition, an exposure area is made with a hard mask to define a surface where pristine BDD is to be exposed.

Electrochemical Properties of the Diamond Fiber Electrode.

Studies are performed to evaluate the general electrochemical characteristics of the all diamond microfiber ex vivo using cyclic voltammetry (CV) and electrochemical impedance spectroscopy (EIS). The fibers are mounted on a PCB stick for proper electrical connection and mechanical stability. The electrochemical impedance of the electrode at 1 kHz is 1.3 MΩ, in an acceptable range for extracellular recording. Background CV i-E curves are completed in 1.0 M $H_2SO_4$ and pH 7.4 phosphate-buffered saline (PBS) buffer to determine both the potential window and the double layer capacitance ($C_{dl}$); the potential window curves are shown in FIG. 13A13. The potential window is found to be approximately 5.0 V in pH 7.4 PBS and approximately 4.0 V in 1.0 M $H_2SO_4$. The calculated double layer capacitance ($C_{dl}$) (data not shown) is 11 µF/cm². CV i-E curves of ferri/ferrocyanide ($Fe(CN)_6^{3-/4-}$), ruthenium hexamine ($Ru(NH_3)_6^{2+/3+}$), and hydroquinone (HQ), are shown in FIG. 13B. In all cases, the diamond microfibers exhibit the trademark sigmoidal response characteristic of microelectrodes, occurring when the radius of the electrode is smaller than that of the diffusion profile of the analyte of interest. The obtained sigmoidal CV shape is especially promising for the $Fe(CN)_6^{3-/4-}$ redox couple, as this electron transfer reaction is known to be sensitive to the diamond electrode surface. FIG. 13C compares the potential window of an MCD-BDD electrode and standard gold, platinum, and glassy carbon electrodes. The BDD electrode exhibits featureless background current and a wider potential window in PBS (approximately 3.8 V), permitting detection of analytes across a wide voltage range without the interference of faradaic background current due to electrochemical oxidation and/or reduction of water.

Ex Vivo Dopamine Sensing by Diamond Electrodes.

The pristine BDD microfibers are characterized for the ability to detect dopamine by traditional CV measurements. Scan rates of 0.05 to 50 V/s are investigated; the data at a scan rate of 1.0 V/s is shown in FIG. 14A. In the dopamine scan rate study, the steady-state current response is observed up to a scan rate of 5.0 V/s (data not shown). At higher scan rates, the transition from steady-state conditions to voltammetric peaks is largely due to the change in diffusive properties.

To effectively detect neurochemical transients in vivo, measurements must be executed on the millisecond (ms) time scale, due to a combination of the neuron firing rate and diffusivity of dopamine into the extracellular space. This is typically done using fast-scan CV (FSCV), a well-established method for real-time monitoring of rapid changes in analyte concentrations at the ms scale. In FSCV, the background charging current stabilizes after repeated cycling of the electrochemical potential, and thus, can be subtracted from the measured faradaic current. The color plot in FIG. 14B shows a time plot of a constant dopamine concentration, where a solid current response from both the oxidation and reduction peaks of dopamine is observed in a stagnant electrochemical cell. This signifies that the pristine BDD fibers exhibit the conductivity needed for FSCV. FIG. 14C shows an individual FSCV of dopamine extracted from the time plot, where the oxidation peak of dopamine shifts positively from FIG. 14A. This slight shift is largely due to the increased electrochemical resistivity of micro-scaled BDD electrodes. However, the increased anodic potential window of the BDD microfiber electrode (compared to competing materials) mitigates the issue of the shift in the DA oxidation potential. In contrast to metal wires and CF electrodes that require specific surface treatments, the diamond electrodes described here show great promise for highly-selective, label-free measurement of dopamine without any surface treatments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An electrode comprising:
   a contact pad comprising boron-doped polycrystalline diamond (BDD);
   a fiber core comprising BDD extending longitudinally from the contact pad from a proximal end that is in direct contact with the contact pad to an opposing distal end; and
   a polycrystalline diamond (PCD) cladding that coats and hermetically seals a first portion of the contact pad and a second portion of the fiber core, wherein
   a third portion of the contact pad and a fourth portion of the fiber core at the distal end of the fiber core are not coated and hermetically sealed by the PCD cladding, and
   the fiber core and the PCD cladding collectively define a longitudinal shank having a width of greater than or equal to about 0.3 µm and less than or equal to about 45 µm and a height of greater than or equal to about 0.45 µm to less than or equal to about 30 µm, wherein BDD of the fourth portion is exposed at the distal end of the longitudinal shank, is pristine BDD, and defines a sensing region, BDD of the third portion is exposed at an outermost surface of the contact pad and defines an electrode lead region, and a plane of the fourth portion is perpendicular to a plane of the third portion.

2. The electrode according to claim 1, wherein the fiber core has a rectangular or square cross-sectional geometry.

3. The electrode according to claim 1, wherein the distal end of the fiber core is blunt.

4. The electrode according to claim 3, wherein the fiber core has a width of greater than or equal to about 0.1 µm to less than or equal to about 25 µm and a height of greater than or equal to about 0.25 µm to less than or equal to about 10 µm.

5. The electrode according to claim 1, wherein the PCD cladding has a thickness of greater than or equal to about 0.1 µm to less than or equal to about 10 µm.

6. The electrode according to claim 5, wherein the PCD cladding is substantially free of pinholes.

7. The electrode according to claim 1, wherein the BDD fiber core has a length of greater than or equal to about 0.5 mm to less than or equal to about 20 mm.

8. The electrode according to claim 1, wherein the BDD fiber core coated with PCD has a diameter that is smaller than the size of a neuron.

9. A fiber comb comprising at least two electrodes according to claim 1, wherein the BDD fiber core of each of the at least two electrodes individually has a length of greater than or equal to about 0.5 mm to less than or equal to about 20 mm, and wherein the at least two electrodes are arranged in a line.

10. The fiber comb according to claim 9, wherein the at least two electrodes are electrically coupled to a ribbon cable.

11. A fiber array comprising at least three electrodes according to claim 1, wherein the BDD fiber core of each of the at least three electrodes individually has a length of greater than or equal to about 1 mm to less than or equal to about 10 mm, and wherein the at least three electrodes are arranged in a three-dimensional pattern.

12. The fiber array according to claim 11, wherein the at least three electrodes extend from, and are electrically coupled to, a circuit substrate.

13. An electrode comprising:
at least one individual electrode comprising:
a contact pad comprising boron-doped polycrystalline diamond (BDD);
a fiber core comprising BDD extending longitudinally from the contact pad from a proximal end that is in direct contact with the contact pad to an opposing distal end; and
a polycrystalline diamond (PCD) cladding that coats and hermetically seals the entire individual electrode except for at least a first portion of the contact pad and a single second portion at the distal end of the fiber core, the single second portion being pristine BDD,
wherein
the distal end of the fiber core having the PCD cladding is configured to be inserted between neurons in a brain or within a single neuron in a brain,
the fiber core and the PCD cladding collectively define a longitudinal shank,
BDD of the first portion is exposed at the distal end of the longitudinal shank, is pristine BDD, and defines a sensing region,
BDD of the single second portion is exposed at an outermost surface of the contact pad and defines an electrode lead region.

14. The electrode according to claim 13, wherein the electrode is:
an electrode comprising one individual electrode;
an electrode comb comprising at least two of the individual electrodes arranged in a line; or
an electrode array comprising at least three of the individual electrodes arranged in a three-dimensional pattern.

15. A method for fabricating an electrode, the method comprising:
depositing a first layer of polycrystalline diamond (PCD) onto a substrate;
depositing a layer of boron-doped polycrystalline diamond (BDD) on the first layer of PCD;
forming the first layer of PCD and the layer of BDD into a pattern, the pattern comprising a first section defining a contact pad and a second section extending longitudinally from the first section from a proximal end to an opposing distal end that defines a fiber core;
depositing a second layer of PCD over the entire layer of BDD, wherein the second layer of PCD contacts the first layer of PCD to coat and hermetically seal a first portion of the contact pad and a second portion of the fiber core, wherein a third portion of the contact pad and a fourth portion of the fiber core are not coated and hermetically sealed by the PCD, to form the electrode; and
removing the electrode from the substrate, wherein
BDD of the fourth portion is exposed at the distal end of a longitudinal shank is pristine BDD, and defines a sensing region of the electrode,
BDD of the third portion is exposed at an outermost surface of the contact pad and defines an electrode lead region, and
the fiber core and the PCD layer collectively define the longitudinal shank.

16. The method according to claim 15, wherein the depositing a second layer of PCD comprises:
depositing a layer of sacrificial photoresist over the layer of BDD and patterning the layer of sacrificial photoresist to expose the third portion of the first section and the fourth portion at the second section at the distal end;
depositing a hard mask comprising tungsten or copper over exposed substrate, BDD, and sacrificial photoresist;
removing a portion of the hard mask that is deposited on the sacrificial photoresist by dissolving the sacrificial photoresist;
depositing the second layer of PCD on areas where there is no hard mask to selectively encapsulate the layer of BDD; and
removing the remaining hard mask to yield the electrode coupled to the substrate by way of the first layer of PCD.

17. The method according to claim 15, wherein the depositing the first layer of PCD onto the substrate and the depositing the layer of BDD on the first layer of PCD are performed by microwave plasma-assisted chemical vapor deposition, hot-filament chemical vapor deposition, or a combination thereof.

18. The method according to claim 15, comprising depositing the second layer of PCD over the entire layer of BDD, except for only the third portion of the first section, and after the removing, exposing the BDD at the fourth portion at the distal end of the fiber core.

19. The method according to claim 15, further comprising:
   integrating the electrode into either a two-dimensional electrode comb or a three-dimensional electrode array.

20. The method according to claim 15, further comprising: removing a portion of the distal end.

* * * * *